US012606631B2

(12) United States Patent
Yan et al.

(10) Patent No.: US 12,606,631 B2
(45) Date of Patent: Apr. 21, 2026

(54) ANTIBODIES WHICH BIND HUMAN ENDOTHELIN RECEPTOR A (ET$_A$R)

(71) Applicant: REMD Biotherapeutics, Inc., Camarillo, CA (US)

(72) Inventors: Hai Yan, Thousand Oaks, CA (US); John Zhang, Camarillo, CA (US)

(73) Assignee: REMD Biotherapeutics Inc, Camarillo, CA (US)

( * ) Notice: Subject to any disclaimer, the term of this patent is extended or adjusted under 35 U.S.C. 154(b) by 727 days.

(21) Appl. No.: 17/926,295

(22) PCT Filed: May 19, 2021

(86) PCT No.: PCT/US2021/033088
§ 371 (c)(1),
(2) Date: Nov. 18, 2022

(87) PCT Pub. No.: WO2021/236724
PCT Pub. Date: Nov. 25, 2021

(65) Prior Publication Data
US 2023/0212300 A1     Jul. 6, 2023

Related U.S. Application Data

(60) Provisional application No. 63/027,465, filed on May 20, 2020.

(51) Int. Cl.
*C07K 16/28*     (2006.01)

(52) U.S. Cl.
CPC ...... *C07K 16/2869* (2013.01); *C07K 2317/24* (2013.01); *C07K 2317/55* (2013.01); *C07K 2317/565* (2013.01); *C07K 2317/92* (2013.01)

(58) Field of Classification Search
CPC ............ C07K 16/2869; C07K 2317/24; C07K 2317/55; C07K 2317/565; C07K 2317/92; C07K 2317/76
See application file for complete search history.

(56) References Cited

U.S. PATENT DOCUMENTS

| | | |
|---|---|---|
| 10,376,581 B2 | 8/2019 | Zhang et al. |
| 2004/0131607 A1 | 7/2004 | Carroll et al. |
| 2014/0057300 A1 | 2/2014 | Hryhorenko et al. |
| 2014/0356364 A1 | 12/2014 | Langermann et al. |
| 2017/0088605 A1 | 3/2017 | Abend et al. |
| 2020/0033338 A1 | 1/2020 | Fairclough et al. |

FOREIGN PATENT DOCUMENTS

| | | |
|---|---|---|
| WO | 2020023679 | 1/2020 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig. M. M. (1995) Methods: A Companion to Methods in Enzymology, 8:83-93.*
Maccallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*
https://www.thermofisher.com > Antibodies > Endothelin 1 (retrieved from the internet Aug. 10, 2025).*
https://www.abcam.com > products > primary-antibodies (retrieved from the internet Aug. 10, 2025).*
Abcam product worksheet Abcam EDNRA monoclonal antibody (M02), clone 2A5, Aug. 25, 2021.
Maguire et al., "Endothelin Receptors and Their Antagonists", Seminars in Nephrology, vol. 35, No. 2, pp. 125-136, Mar. 2015.

* cited by examiner

*Primary Examiner* — Robert S Landsman
(74) *Attorney, Agent, or Firm* — Craig A Crandall, APC; Craig A Crandall

(57) ABSTRACT

This application provides isolated antibodies, and antigen-binding fragments thereof, that specifically bind endothelin A receptor (ET$_A$R). These ET$_A$R antibodies, or antigen-binding fragments thereof, have a high affinity for ET$_A$R, function to effectively block ET-1 binding to ET$_A$R, are less immunogenic compared to their unmodified parent antibodies in a given species (e.g., in a human), and can be used to treat ET$_A$R-associated disorders. Importantly, compared to small molecule ET$_A$R antagonists, the antibodies of the present invention have advantages of longer serum half-life, higher target specificity, thereby limiting the risk of off-target toxicity and improving therapeutic window.

7 Claims, 3 Drawing Sheets

Specification includes a Sequence Listing.

17: 312A10E5 (A3)
21: 336D8G9 (A2)

17: 312A10E5 (A3)
21: 336D8G9 (A2)

SEQUENCE LISTING

<160> NUMBER OF SEQ ID NOS: 50

<210> SEQ ID NO 1
<211> LENGTH: 427
<212> TYPE: PRT
<213> ORGANISM: Homo sapiens

<400> SEQUENCE: 1

```
Met Glu Thr Leu Cys Leu Arg Ala Ser Phe Trp Leu Ala Leu Val Gly
1               5                   10                  15

Cys Val Ile Ser Asp Asn Pro Glu Arg Tyr Ser Thr Asn Leu Ser Asn
            20                  25                  30

His Val Asp Asp Phe Thr Thr Phe Arg Gly Thr Glu Leu Ser Phe Leu
        35                  40                  45

Val Thr Thr His Gln Pro Thr Asn Leu Val Leu Pro Ser Asn Gly Ser
    50                  55                  60

Met His Asn Tyr Cys Pro Gln Gln Thr Lys Ile Thr Ser Ala Phe Lys
65                  70                  75                  80

Tyr Ile Asn Thr Val Ile Ser Cys Thr Ile Phe Ile Val Gly Met Val
                85                  90                  95

Gly Asn Ala Thr Leu Leu Arg Ile Ile Tyr Gln Asn Lys Cys Met Arg
                100                 105                 110

Asn Gly Pro Asn Ala Leu Ile Ala Ser Leu Ala Leu Gly Asp Leu Ile
            115                 120                 125

Tyr Val Val Ile Asp Leu Pro Ile Asn Val Phe Lys Leu Leu Ala Gly
    130                 135                 140

Arg Trp Pro Phe Asp His Asn Asp Phe Gly Val Phe Leu Cys Lys Leu
145                 150                 155                 160

Phe Pro Phe Leu Gln Lys Ser Ser Val Gly Ile Thr Val Leu Asn Leu
                165                 170                 175

Cys Ala Leu Ser Val Asp Arg Tyr Arg Ala Val Ala Ser Trp Ser Arg
                180                 185                 190

Val Gln Gly Ile Gly Ile Pro Leu Val Thr Ala Ile Glu Ile Val Ser
            195                 200                 205

Ile Trp Ile Leu Ser Phe Ile Leu Ala Ile Pro Glu Ala Ile Gly Phe
    210                 215                 220

Val Met Val Pro Phe Glu Tyr Arg Gly Glu Gln His Lys Thr Cys Met
225                 230                 235                 240

Leu Asn Ala Thr Ser Lys Phe Met Glu Phe Tyr Gln Asp Val Lys Asp
                245                 250                 255

Trp Trp Leu Phe Gly Phe Tyr Phe Cys Met Pro Leu Val Cys Thr Ala
                260                 265                 270

Ile Phe Tyr Thr Leu Met Thr Cys Glu Met Leu Asn Arg Arg Asn Gly
            275                 280                 285

Ser Leu Arg Ile Ala Leu Ser Glu His Leu Lys Gln Arg Arg Glu Val
    290                 295                 300

Ala Lys Thr Val Phe Cys Leu Val Val Ile Phe Ala Leu Cys Trp Phe
305                 310                 315                 320

Pro Leu His Leu Ser Arg Ile Leu Lys Lys Thr Val Tyr Asn Glu Met
                325                 330                 335

Asp Lys Asn Arg Cys Glu Leu Leu Ser Phe Leu Leu Leu Met Asp Tyr
                340                 345                 350

Ile Gly Ile Asn Leu Ala Thr Met Asn Ser Cys Ile Asn Pro Ile Ala
            355                 360                 365
```

-continued

```
Leu Tyr Phe Val Ser Lys Lys Phe Lys Asn Cys Phe Gln Ser Cys Leu
    370             375             380

Cys Cys Cys Cys Tyr Gln Ser Lys Ser Leu Met Thr Ser Val Pro Met
385             390             395             400

Asn Gly Thr Ser Ile Gln Trp Lys Asn His Asp Gln Asn Asn His Asn
            405             410             415

Thr Asp Arg Ser Ser His Lys Asp Ser Met Asn
            420             425

<210> SEQ ID NO 2
<211> LENGTH: 5
<212> TYPE: PRT
<213> ORGANISM: Mus musculus

<400> SEQUENCE: 2

Ser Tyr Trp Met Asn
1               5

<210> SEQ ID NO 3
<211> LENGTH: 5
<212> TYPE: PRT
<213> ORGANISM: Mus musculus

<400> SEQUENCE: 3

Asp Tyr Tyr Ile His
1               5

<210> SEQ ID NO 4
<211> LENGTH: 5
<212> TYPE: PRT
<213> ORGANISM: Mus musculus

<400> SEQUENCE: 4

Asn Tyr Gly Met Ser
1               5

<210> SEQ ID NO 5
<211> LENGTH: 17
<212> TYPE: PRT
<213> ORGANISM: Mus musculus

<400> SEQUENCE: 5

Gln Ile Tyr Pro Gly Asn Gly Asp Thr Asn Tyr Asn Gly Lys Phe Arg
1               5               10              15

Gly

<210> SEQ ID NO 6
<211> LENGTH: 17
<212> TYPE: PRT
<213> ORGANISM: Mus musculus

<400> SEQUENCE: 6

Arg Ile Asp Pro Glu Asp Gly Asp Thr Glu Tyr Ala Pro Lys Phe Gln
1               5               10              15

Gly

<210> SEQ ID NO 7
<211> LENGTH: 17
<212> TYPE: PRT
<213> ORGANISM: Mus musculus

<400> SEQUENCE: 7
```

-continued

```
Trp Ile Asn Thr Tyr Ser Gly Glu Ser Thr Tyr Ala Asp Asp Phe Lys
1               5                   10                  15

Gly

<210> SEQ ID NO 8
<211> LENGTH: 6
<212> TYPE: PRT
<213> ORGANISM: Mus musculus

<400> SEQUENCE: 8

Arg Gly Ser Leu Asp Tyr
1               5

<210> SEQ ID NO 9
<211> LENGTH: 12
<212> TYPE: PRT
<213> ORGANISM: Mus musculus

<400> SEQUENCE: 9

Gly Tyr Thr Phe Thr Asn Trp Tyr Ser Asn Ser Tyr
1               5                   10

<210> SEQ ID NO 10
<211> LENGTH: 10
<212> TYPE: PRT
<213> ORGANISM: Mus musculus

<400> SEQUENCE: 10

Ser Leu Asn Arg Asp Thr Trp Phe Thr Tyr
1               5                   10

<210> SEQ ID NO 11
<211> LENGTH: 16
<212> TYPE: PRT
<213> ORGANISM: Mus musculus

<400> SEQUENCE: 11

Lys Ser Ser His Ser Leu Val His Ser Asn Gly Asp Thr Tyr Leu His
1               5                   10                  15

<210> SEQ ID NO 12
<211> LENGTH: 16
<212> TYPE: PRT
<213> ORGANISM: Mus musculus

<400> SEQUENCE: 12

Arg Ser Ser Gln Ser Leu Val His Ser Asn Gly Asn Thr Tyr Leu His
1               5                   10                  15

<210> SEQ ID NO 13
<211> LENGTH: 14
<212> TYPE: PRT
<213> ORGANISM: Mus musculus

<400> SEQUENCE: 13

Arg Ser Ile Thr Gly Ala Val Thr Thr Ser Asn Tyr Ala Asn
1               5                   10

<210> SEQ ID NO 14
<211> LENGTH: 7
<212> TYPE: PRT
<213> ORGANISM: Mus musculus

<400> SEQUENCE: 14
```

-continued

```
Lys Val Ser Asn Arg Phe Ser
1               5

<210> SEQ ID NO 15
<211> LENGTH: 7
<212> TYPE: PRT
<213> ORGANISM: Mus musculus

<400> SEQUENCE: 15

Gly Thr Asn Asn Arg Ala Pro
1               5

<210> SEQ ID NO 16
<211> LENGTH: 9
<212> TYPE: PRT
<213> ORGANISM: Mus musculus

<400> SEQUENCE: 16

Ser Gln Thr Thr Tyr Val Pro Tyr Thr
1               5

<210> SEQ ID NO 17
<211> LENGTH: 9
<212> TYPE: PRT
<213> ORGANISM: Mus musculus

<400> SEQUENCE: 17

Ser Gln Ser Thr His Val Pro Tyr Thr
1               5

<210> SEQ ID NO 18
<211> LENGTH: 9
<212> TYPE: PRT
<213> ORGANISM: Mus musculus

<400> SEQUENCE: 18

Ala Leu Trp Tyr Ser Asn His Trp Val
1               5

<210> SEQ ID NO 19
<211> LENGTH: 115
<212> TYPE: PRT
<213> ORGANISM: Mus musculus

<400> SEQUENCE: 19

Gln Val Gln Leu Gln Gln Ser Gly Ala Glu Leu Val Arg Pro Gly Ser
1               5                   10                  15

Ser Val Arg Ile Ser Cys Lys Ala Phe Asp Tyr Ala Phe Ser Ser Tyr
            20                  25                  30

Trp Met Asn Trp Val Lys Gln Arg Pro Gly Gln Asp Leu Glu Trp Ile
        35                  40                  45

Gly Gln Ile Tyr Pro Gly Asn Gly Asp Thr Asn Tyr Asn Gly Lys Phe
    50                  55                  60

Arg Gly Lys Ala Ser Leu Thr Ala Asp Lys Ser Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Arg Gly Ser Leu Asp Tyr Trp Gly Gln Gly Thr Ser Val Thr
            100                 105                 110

Val Ser Ser
        115
```

-continued

<210> SEQ ID NO 20
<211> LENGTH: 345
<212> TYPE: DNA
<213> ORGANISM: Mus musculus

<400> SEQUENCE: 20
caggttcagc tgcagcagtc tggggctgag ttggtgaggc ctgggtcctc agtgaggatt      60
tcctgcaagg cttttgacta tgcattcagt agctactgga tgaactgggt gaagcagagg     120
cctggacagg atcttgagtg gattggacag atttatcctg gaaatggtga tactaactac     180
aatggaaagt tcaggggtaa agcctcactg actgcagaca atcctccag cacagcctac      240 atgcacctca gcagcctaac atctgaggac tctgcggtct atttctgtgc aagacggggg     300
tctttggact actggggtca aggaacctca gtcaccgtct cctca                     345

<210> SEQ ID NO 21
<211> LENGTH: 112
<212> TYPE: PRT
<213> ORGANISM: Mus musculus

<400> SEQUENCE: 21

Asp Val Val Met Thr Gln Ile Pro Leu Ser Leu Pro Val Ser Leu Gly
1               5                   10                  15

Asp Gln Ser Ser Ile Ser Cys Lys Ser Ser His Ser Leu Val His Ser
            20                  25                  30

Asn Gly Asp Thr Tyr Leu His Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Thr Gly Ser Gly Ser Gly Thr Glu Phe Thr Leu Lys Ile
65                  70                  75                  80

Ser Arg Val Glu Ala Glu Asp Leu Gly Val Tyr Phe Cys Ser Gln Thr
                85                  90                  95

Thr Tyr Val Pro Tyr Thr Phe Gly Gly Gly Thr Lys Leu Glu Ile Lys
            100                 105                 110

<210> SEQ ID NO 22
<211> LENGTH: 336
<212> TYPE: DNA
<213> ORGANISM: Mus musculus

<400> SEQUENCE: 22
gatgtggtga tgacccaaat tccactctcc ctgcctgtca gtcttggaga tcaatcctcc       60
atctcttgca aatctagtca tagccttgta catagtaatg gagacaccta tttacattgg      120
ttcctgcaga agccaggcca gtctccaaag ctcctgatct acaaagtctc caaccgattt      180 tctgggtcc cagacaggtt cactggcagt ggttcaggga cagagttcac actcaagatc       240
agcagagtgg aggctgagga tctgggagtt tatttctgct ctcaaactac atatgttccg      300
tacacgttcg gaggggggac caagctggaa ataaaa                                336

<210> SEQ ID NO 23
<211> LENGTH: 116
<212> TYPE: PRT
<213> ORGANISM: Mus musculus

<400> SEQUENCE: 23

Glu Val Gln Leu Gln Gln Ser Gly Ala Glu Leu Val Arg Pro Gly Ala
1               5                   10                  15

```
Ser Val Lys Leu Ser Cys Pro Ala Ser Gly Phe Thr Ile Lys Asp Tyr
            20                  25                  30

Tyr Ile His Trp Val Lys Gln Arg Pro Glu Gln Gly Leu Glu Trp Ile
            35                  40                  45

Gly Arg Ile Asp Pro Glu Asp Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Thr Ser Asn Trp Tyr Ser Asn Ser Tyr Trp Gly Gln Gly Thr Thr Leu
            100                 105                 110

Thr Val Ser Ser
        115
```

<210> SEQ ID NO 24
<211> LENGTH: 348
<212> TYPE: DNA
<213> ORGANISM: Mus musculus

<400> SEQUENCE: 24

```
gaggttcagc tgcagcagtc tggggcagag cttgtgaggc caggggcctc agtcaagttg      60
tcctgcccag cttctggctt caccattaaa gactactata tacactgggt gaagcagagg     120
cctgagcagg gcctggagtg gattggaagg attgatcctg aggatggtga tactgaatat     180
gccccgaagt tccagggcaa ggccactatg actgcagaca catcctccaa cacagcctac     240
ctgcacctca gcagcctgac atctgaggac actgccgtct attactgtac ttcaaactgg     300
tatagtaact cctactgggg ccaaggcacc actctcacag tctcctca                 348
```

<210> SEQ ID NO 25
<211> LENGTH: 112
<212> TYPE: PRT
<213> ORGANISM: Mus musculus

<400> SEQUENCE: 25

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 26
<211> LENGTH: 336
<212> TYPE: DNA
<213> ORGANISM: Mus musculus

<400> SEQUENCE: 26

-continued

```
gatgttgtga tgacccaaac tccactctcc ctgcctgtca gtcttggaga tcaagcctcc        60
atctcttgca gatctagtca gagccttgta cacagtaatg aaacaccta tttacattgg        120 tacctgcaaa agccaggcca gtctccaaag gtcctgatct acaaagtttc caaccgattt        180
tctggggtcc cagacaggtt cagtggcagt ggatcaggga cagatttcac actcaagatc        240
agcagagtgg aggctgagga tctgggagtt tatttctgct ctcaaagtac acatgttccg        300
tatacgttcg gaggggggac caagctggaa ataaaa                                  336
```

```
<210> SEQ ID NO 27
<211> LENGTH: 119
<212> TYPE: PRT
<213> ORGANISM: Mus musculus

<400> SEQUENCE: 27

Gln Ile Gln Leu Val Gln Ser Gly Pro Asp Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Ser Trp Val Lys Gln Ala Pro Gly Lys Gly Leu Lys Trp Met
            35                  40                  45

Gly Trp Ile Asn Thr Tyr Ser Gly Glu Ser Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Leu Asn Arg Asp Thr Trp Phe Thr Tyr Trp Gly Gln Gly
            100                 105                 110

Thr Leu Val Thr Val Ser Ala
        115
```

```
<210> SEQ ID NO 28
<211> LENGTH: 357
<212> TYPE: DNA
<213> ORGANISM: Mus musculus

<400> SEQUENCE: 28
cagatccagt tggtacagtc tggacctgac ctgaagaagc ctggagagac agtcaagatc        60
tcctgcaagg cttctgggta taccttcaca aactatggaa tgagctgggt gaaacaggct        120
ccaggaaagg gtttaaagtg gatgggctgg ataaacacct attctggaga gtcaacatat        180
gctgatgact tcaagggacg gtttgccttc tctttggaaa cctctgccag cactgcctat        240
ttgcagatca acaacctcaa aaatgaggac acggctacat atttctgtgc aagatccctc        300
aaccgggaca cctggtttac ttactggggc caagggactc tggtcactgt ctctgca          357
```

```
<210> SEQ ID NO 29
<211> LENGTH: 109
<212> TYPE: PRT
<213> ORGANISM: Mus musculus

<400> SEQUENCE: 29

Gln Ala Val Val Thr Gln Glu Ser Ala Leu Ser Thr Ser Pro Gly Glu
1               5                   10                  15

Thr Val Thr Leu Thr Cys Arg Ser Ile Thr Gly Ala Val Thr Thr Ser
                20                  25                  30

Asn Tyr Ala Asn Trp Val Gln Glu Lys Pro Asp His Leu Phe Thr Gly
```

```
              35                    40                    45
Leu Ile Gly Gly Thr Asn Asn Arg Ala Pro Gly Val Pro Ala Arg Phe
   50                    55                    60

Ser Gly Ser Leu Ile Gly Asp Lys Ala Ala Leu Thr Ile Thr Gly Ala
65                    70                    75                    80

Gln Thr Glu Asp Glu Ala Ile Tyr Phe Cys Ala Leu Trp Tyr Ser Asn
              85                    90                    95

His Trp Val Phe Gly Gly Gly Thr Lys Leu Thr Val Leu
              100                   105
```

```
<210> SEQ ID NO 30
<211> LENGTH: 327
<212> TYPE: DNA
<213> ORGANISM: Mus musculus

<400> SEQUENCE: 30
caggctgttg tgactcagga atctgcactc tccacatcac ctggtgaaac agtcacactc        60
acttgtcgct caattactgg ggctgttaca actagtaact atgccaactg ggtccaagaa       120
aaaccagatc atttgttcac tggtctaata ggtggtacca acaaccgagc tccaggtgtt       180
cctgccagat tctcaggctc cctgattgga gacaaggctg ccctcaccat cacaggggca       240
cagactgagg atgaggcaat atatttctgt gctctatggt acagcaacca ctgggtgttc       300
ggtggaggaa ccaaactgac tgtccta                                          327
```

```
<210> SEQ ID NO 31
<211> LENGTH: 119
<212> TYPE: PRT
<213> ORGANISM: Artificial
<220> FEATURE:
<223> OTHER INFORMATION: Heavy chain variable region amino acid sequence
      of a murine-human chimeric antibody

<400> SEQUENCE: 31

Gln Val Gln Leu Val Gln Ser Gly Ala Glu Val Lys Lys Pro Gly Ala
1                    5                    10                    15

Ser Val Lys Val Ser Cys Lys Ala Ser Gly Tyr Thr Phe Thr Asn Tyr
              20                    25                    30

Gly Met Ser Trp Val Arg Gln Ala Pro Gly Gln Gly Leu Glu Trp Met
              35                    40                    45

Gly Trp Ile Asn Thr Tyr Ser Gly Glu Ser Thr Tyr Ala Asp Asp Phe
   50                    55                    60

Lys Gly Arg Val Thr Met Thr Thr Asp Thr Ser Thr Ser Thr Ala Tyr
65                    70                    75                    80

Met Glu Leu Arg Ser Leu Arg Ser Asp Asp Thr Ala Val Tyr Tyr Cys
              85                    90                    95

Ala Arg Ser Leu Asn Arg Asp Thr Trp Phe Thr Tyr Trp Gly Gln Gly
              100                   105                   110

Thr Leu Val Thr Val Ser Ser
              115
```

```
<210> SEQ ID NO 32
<211> LENGTH: 109
<212> TYPE: PRT
<213> ORGANISM: Artificial
<220> FEATURE:
<223> OTHER INFORMATION: Light chain variable region amino acid sequence
      of a murine-human chimeric antibody

<400> SEQUENCE: 32
```

-continued

```
Gln Thr Val Val Thr Gln Glu Pro Ser Phe Ser Val Ser Pro Gly Gly
1               5                   10                  15

Thr Val Thr Leu Thr Cys Arg Ser Ile Thr Gly Ala Val Thr Thr Ser
                20                  25                  30

Asn Tyr Ala Asn Trp Tyr Gln Gln Thr Pro Gly Gln Ala Pro Arg Thr
            35                  40                  45

Leu Ile Tyr Gly Thr Asn Asn Arg Ala Pro Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

His Trp Val Phe Gly Gly Gly Thr Lys Leu Thr Val Leu
            100                 105
```

```
<210> SEQ ID NO 33
<211> LENGTH: 119
<212> TYPE: PRT
<213> ORGANISM: Artificial
<220> FEATURE:
<223> OTHER INFORMATION: Humanized heavy chain variable region amino
      acid sequence

<400> SEQUENCE: 33
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Ser Trp Val Arg Gln Ala Pro Gly Gln Gly Leu Glu Trp Met
            35                  40                  45

Gly Trp Ile Asn Thr Tyr Ser Gly Glu Ser Thr Tyr Ala Asp Asp Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Leu Asn Arg Asp Thr Trp Phe Thr Tyr Trp Gly Gln Gly
            100                 105                 110

Thr Leu Val Thr Val Ser Ser
        115
```

```
<210> SEQ ID NO 34
<211> LENGTH: 119
<212> TYPE: PRT
<213> ORGANISM: Artificial
<220> FEATURE:
<223> OTHER INFORMATION: Humanized heavy chain variable region amino
      acid sequence

<400> SEQUENCE: 34
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Ser Trp Val Arg Gln Ala Pro Gly Gln Gly Leu Glu Trp Met
            35                  40                  45

Gly Trp Ile Asn Thr Tyr Ser Gly Glu Ser Thr Tyr Ala Asp Asp Phe
        50                  55                  60
```

Lys Gly Arg Phe Thr Met Thr Leu Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Ser Leu Asn Arg Asp Thr Trp Phe Thr Tyr Trp Gly Gln Gly
            100                 105                 110

Thr Leu Val Thr Val Ser Ser
        115

<210> SEQ ID NO 35
<211> LENGTH: 119
<212> TYPE: PRT
<213> ORGANISM: Artificial
<220> FEATURE:
<223> OTHER INFORMATION: Humanized heavy chain variable region amino
      acid sequence

<400> SEQUENCE: 35

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asn Tyr
                20                  25                  30

Gly Met Ser Trp Val Arg Gln Ala Pro Gly Gln Gly Leu Glu Trp Met
            35                  40                  45

Gly Trp Ile Asn Thr Tyr Ser Gly Glu Ser Thr Tyr Ala Asp Asp Phe
            50                  55                  60

Lys Gly Arg Phe Thr Phe Thr Leu Asp Thr Ser Thr Ser Thr Ala Tyr
65                  70                  75                  80

Met Glu Leu Arg Ser Leu Arg Ser Asp Asp Thr Ala Thr Tyr Phe Cys
                85                  90                  95

Ala Arg Ser Leu Asn Arg Asp Thr Trp Phe Thr Tyr Trp Gly Gln Gly
            100                 105                 110

Thr Leu Val Thr Val Ser Ser
        115

<210> SEQ ID NO 36
<211> LENGTH: 109
<212> TYPE: PRT
<213> ORGANISM: Artificial
<220> FEATURE:
<223> OTHER INFORMATION: Humanized light chain variable region amino
      acid sequence

<400> SEQUENCE: 36

Gln Thr Val Val Thr Gln Glu Pro Ser Phe Ser Val Ser Pro Gly Gly
1                   5                   10                  15

Thr Val Thr Leu Thr Cys Arg Ser Ile Thr Gly Ala Val Thr Thr Ser
                20                  25                  30

Asn Tyr Ala Asn Trp Tyr Gln Gln Thr Pro Gly Gln Ala Pro Arg Gly
            35                  40                  45

Leu Ile Gly Gly Thr Asn Asn Arg Ala Pro Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Ala Leu Trp Tyr Ser Asn
                85                  90                  95

His Trp Val Phe Gly Gly Gly Thr Lys Leu Thr Val Leu
            100                 105

```
<210> SEQ ID NO 37
<211> LENGTH: 109
<212> TYPE: PRT
<213> ORGANISM: Artificial
<220> FEATURE:
<223> OTHER INFORMATION: Humanized light chain variable region amino
      acid sequence

<400> SEQUENCE: 37

Gln Thr Val Val Thr Gln Glu Pro Ser Phe Ser Val Ser Pro Gly Gly
1               5                   10                  15

Thr Val Thr Leu Thr Cys Arg Ser Ile Thr Gly Ala Val Thr Thr Ser
            20                  25                  30

Asn Tyr Ala Asn Trp Val Gln Glu Thr Pro Gly Gln Ala Pro Arg Gly
        35                  40                  45

Leu Ile Gly Gly Thr Asn Asn Arg Ala Pro Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ala Asp Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 38
<211> LENGTH: 449
<212> TYPE: PRT
<213> ORGANISM: Artificial
<220> FEATURE:
<223> OTHER INFORMATION: Humanized heavy chain amino acid sequence

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Glu Ser Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Leu Asn Arg Asp Thr Trp Phe Thr Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
    435                 440                 445

Lys
```

<210> SEQ ID NO 39
<211> LENGTH: 1347
<212> TYPE: DNA
<213> ORGANISM: Artificial
<220> FEATURE:
<223> OTHER INFORMATION: Humanized heavy chain nucleic acid sequence

<400> SEQUENCE: 39

```
caggtgcagc tggtgcagtc tggagcagag gtgaagaagc caggagcctc tgtgaaggtg      60
agctgcaagg cctccggcta caccttcaca aactatggca tgagctgggt gcggcaggca     120
cctggacagg gactggagtg gatgggctgg atcaatacat actccggcga gtctacctat     180
gccgacgact tcaagggcag ggtgacaatg accacagaca cctctacaag caccgcctac     240
atggagctgc ggagcctgag atccgacgat accgccgtgt actattgtgc caggtccctg     300
aaccgcgata catggttcac ctattgggggc agggcacac tggtgaccgt gagctccgcc      360
agcaccaagg gcccttccgt gtttccactg gcccctcct ctaaatccac atctggcggc     420
accgccgccc tgggctgtct ggtgaaggac tacttcccag agcctgtgac agtgtcctgg     480
aactctggcg ccctgacatc cggcgtgcac acatttccag ccgtgctgca gagctccggc     540
ctgtacagcc tgtctagcgt ggtgacagtg ccctcctcta gcctgggcac acagacctat     600
```

```
atctgcaacg tgaatcacaa gccaagcaat accaaggtgg acaagaaggt ggagcccaag    660
tcctgtgata agacacacac ctgcccccct tgtcctgctc ccgagctgct gggcggccct    720
agcgtgttcc tgtttccacc caagcctaag acaccctga tgatctcccg gacacccgag      780
gtgacctgcg tggtggtgga cgtgtctcac gaggatcctg aggtgaagtt caactggtat    840
gtggatggcg tggaggtgca caatgccaag accaagccca gagaggagca gtacaactct    900
acatataggg tggtgagcgt gctgaccgtg ctgcaccagg actggctgaa cggcaaggag    960
tataagtgca aggtgtccaa taaggccctg cccgccccca tcgagaagac aatcagcaag    1020
gccaagggcc agcctcggga gccacaggtg tacaccctgc ctccatccag agacgagctg    1080
acaaagaacc aggtgtctct gacatgtctg gtgaagggct ctatcctag cgatatcgcc      1140 gtggagtggg agtccaatgg ccagccagag aacaattaca agaccacacc ccctgtgctg    1200
gactccgatg gctccttctt tctgtattcc aagctgaccg tggataagtc tcggtggcag    1260
cagggcaacg tgttcagctg ttccgtgatg cacgaagccc tgcataatca ctatactcag    1320
aaatccctgt ccctgtcacc tggaaag                                        1347
```

<210> SEQ ID NO 40
<211> LENGTH: 215
<212> TYPE: PRT
<213> ORGANISM: Artificial
<220> FEATURE:
<223> OTHER INFORMATION: Humanized light chain amino acid sequence

<400> SEQUENCE: 40

```
Gln Thr Val Val Thr Gln Glu Pro Ser Phe Ser Val Ser Pro Gly Gly
1               5                   10                  15

Thr Val Thr Leu Thr Cys Arg Ser Ile Thr Gly Ala Val Thr Thr Ser
            20                  25                  30

Asn Tyr Ala Asn Trp Val Gln Glu Thr Pro Gly Gln Ala Pro Arg Gly
        35                  40                  45

Leu Ile Gly Gly Thr Asn Asn Arg Ala Pro Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ala Asp Tyr Phe Cys Ala Leu Trp Tyr Ser Asn
                85                  90                  95

His Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 41
<211> LENGTH: 670
<212> TYPE: DNA
<213> ORGANISM: Artificial
<220> FEATURE:
<223> OTHER INFORMATION: Humanized light chain nucleic acid sequence

<400> SEQUENCE: 41
cagacagtgg tgacccagga gcctagcttc tccgtgtctc caggaggaac cgtgacactg      60
acctgcaggt ctatcacagg cgccgtgacc acaagcaact acgccaattg ggtgcaggag     120
acaccaggac aggcaccaag gggactgatc ggaggaacca acaatagggc caccaggagtg    180 cctgaccggt tcagcggatc catcctggga aacaaggccg ccctgacaat caccggagca     240
caggcagacg atgaggcaga ttacttctgt gccctgtggt attccaatca ctgggtgttt     300
ggcggcggca caaagctgac cgtgctgggg cagcccaagg ccgctcctag cgtgacactg     360
tttccccctt cctccgagga gctgcaggcc aacaaggcca ccctggtgtg cctgatctcc     420
gacttctatc ctggcgccgt gacagtggcc tggaaggctg attctagccc agtgaaggct     480
ggcgtggaga ccacaacccc ctccaagcag tctaacaata gtatgccgc ttcctcttac      540 ctgagcctga caccagagca gtggaagtcc caccggtctt acagctgcca ggtcactcac     600
gaaggctcta ccgtggaaaa gacagtcgca cccaccgaat gctcatgata agcttaaggg     660
ttcgatccct                                                            670

<210> SEQ ID NO 42
<211> LENGTH: 449
<212> TYPE: PRT
<213> ORGANISM: Artificial
<220> FEATURE:
<223> OTHER INFORMATION: Humanized heavy chain amino acid sequence

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Glu Ser Thr Tyr Ala Asp Asp Phe
    50                  55                  60

Lys Gly Arg Phe Thr Met Thr Leu Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Ser Leu Asn Arg Asp Thr Trp Phe Thr Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 43
<211> LENGTH: 1347
<212> TYPE: DNA
<213> ORGANISM: Artificial
<220> FEATURE:
<223> OTHER INFORMATION: Humanized heavy chain nucleic acid sequence

<400> SEQUENCE: 43

```
caggtgcagc tggtgcagtc tggagcagag gtgaagaagc caggagcctc tgtgaaggtg      60
agctgcaagg cctccggcta caccttcaca aactatggca tgagctgggt gcggcaggca     120
cctggacagg gactggagtg gatgggctgg atcaatacat actccggcga gtctacctat     180
gccgacgatt tcaagggcag gtttaccatg acactggaca cctctacaag caccgcctac     240
atggagctgc ggagcctgag atccgacgat acagccgtgt atttctgtgc caggtccctg     300
aaccgcgata catggtttac ctactggggc caggcacac tggtgaccgt gagctccgcc     360
agcaccaagg gcccttccgt gtttccactg gcccctcct ctaaatccac atctggcggc     420
accgccgccc tggctgtgtct ggtgaaggac tacttcccag agcctgtgac agtgtcctgg     480
aactctggcg ccctgacatc cggcgtgcac acatttccag ccgtgctgca gagctccggc     540
```

```
ctgtacagcc tgtctagcgt ggtgacagtg ccctcctcta gcctgggcac acagacctat   600
atctgcaacg tgaatcacaa gccaagcaat accaaggtgg acaagaaggt ggagcccaag   660
tcctgtgata agacacacac ctgcccccct tgtcctgctc ccgagctgct gggcggccct   720
agcgtgttcc tgtttccacc caagcctaag gacacccctga tgatctcccg gacacccgag   780
gtgacctgcg tggtggtgga cgtgtctcac gaggatcctg aggtgaagtt caactggtat   840
gtggatggcg tggaggtgca caatgccaag accaagccca gagaggagca gtacaactct   900
acatataggg tggtgagcgt gctgaccgtg ctgcaccagg actggctgaa cggcaaggag   960
tataagtgca aggtgtccaa taaggccctg cccgccccca tcgagaagac aatcagcaag  1020
gccaagggcc agcctcggga gccacaggtg tacaccctgc ctccatccag agacgagctg  1080
acaaagaacc aggtgtctct gacatgtctg gtgaagggct ctatcctag cgatatcgcc  1140 gtggagtggg agtccaatgg ccagccagag aacaattaca gaccacaacc ccctgtgctg  1200
gactccgatg gctccttctt tctgtattcc aagctgaccg tggataagtc tcggtggcag  1260
cagggcaacg tgttcagctg ttccgtgatg cacgaagccc tgcataatca ctatactcag  1320
aaatccctgt ccctgtcacc tggaaag                                      1347
```

<210> SEQ ID NO 44
<211> LENGTH: 449
<212> TYPE: PRT
<213> ORGANISM: Artificial
<220> FEATURE:
<223> OTHER INFORMATION: Humanized heavy chain amino acid sequence

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Glu Ser Thr Tyr Ala Asp Asp Phe
    50                  55                  60

Lys Gly Arg Phe Thr Phe Thr Leu Asp Thr Ser Thr Ser Thr Ala Tyr
65                  70                  75                  80

Met Glu Leu Arg Ser Leu Arg Ser Asp Asp Thr Ala Thr Tyr Phe Cys
                85                  90                  95

Ala Arg Ser Leu Asn Arg Asp Thr Trp Phe Thr Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225             230             235             240

Ser Val Phe Leu Phe Pro Pro Lys Pro Lys Asp Thr Leu Met Ile Ser
                245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
        290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val Ser Leu Thr
            355             360             365

Cys Leu Val Lys Gly Phe Tyr Pro Ser Asp Ile Ala Val Glu Trp Glu
        370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Lys
```

```
<210> SEQ ID NO 45
<211> LENGTH: 1347
<212> TYPE: DNA
<213> ORGANISM: Artificial
<220> FEATURE:
<223> OTHER INFORMATION: Humanized heavy chain nucleic acid sequence

<400> SEQUENCE: 45
caggtgcagc tggtgcagtc tggagcagag gtgaagaagc caggagcctc tgtgaaggtg      60
agctgcaagg cctccggcta caccttcaca aactatggca tgagctgggt gcggcaggca     120
cctggacagg gactggagtg gatgggctgg atcaatacat actccggcga gtctacctat     180
gccgacgact tcaagggcag gttcaccttt acactggaca cctctacaag caccgcctac     240
atggagctgc ggagcctgag atccgacgat acagccacct atttctgtgc caggtccctg     300
aaccgcgata catggtttac ctactggggc caggcacac tggtgaccgt gagctccgcc     360
agcaccaagg gcccttccgt gtttccactg gccccctcct ctaaatccac atctggcggc     420
accgccgccc tgggctgtct ggtgaaggac tacttcccag agcctgtgac agtgtcctgg     480
aactctggcg ccctgacatc cggcgtgcac acatttccag ccgtgctgca gagctccggc     540
ctgtacagcc tgtctagcgt ggtgacagtg ccctcctcta gcctgggcac acagacctat     600
atctgcaacg tgaatcacaa gccaagcaat accaaggtgg acaagaaggt ggagcccaag     660
tcctgtgata gacacacac ctgcccccct tgtcctgctc ccgagctgct gggcggccct      720
```

```
agcgtgttcc tgtttccacc caagcctaag gacaccctga tgatctcccg gacacccgag      780
gtgacctgcg tggtggtgga cgtgtctcac gaggatcctg aggtgaagtt caactggtat      840
gtggatggcg tggaggtgca caatgccaag accaagccca gagaggagca gtacaactct      900
acatataggg tggtgagcgt gctgaccgtg ctgcaccagg actggctgaa cggcaaggag      960
tataagtgca aggtgtccaa taaggccctg cccgccccca tcgagaagac aatcagcaag     1020
gccaagggcc agcctcggga gccacaggtg tacaccctgc ctccatccag agacgagctg     1080
acaaagaacc aggtgtctct gacatgtctg gtgaaggggct tctatcctag cgatatcgcc     1140
gtggagtggg agtccaatgg ccagccagag aacaattaca agaccacacc ccctgtgctg     1200
gactccgatg gctccttctt tctgtattcc aagctgaccg tggataagtc tcggtggcag     1260
cagggcaacg tgttcagctg ttccgtgatg cacgaagccc tgcataatca ctatactcag     1320
aaatccctgt ccctgtcacc tggaaag                                        1347
```

<210> SEQ ID NO 46
<211> LENGTH: 215
<212> TYPE: PRT
<213> ORGANISM: Artificial
<220> FEATURE:
<223> OTHER INFORMATION: Humanized light chain amino acid sequence

<400> SEQUENCE: 46

```
Gln Thr Val Val Thr Gln Glu Pro Ser Phe Ser Val Ser Pro Gly Gly
1               5                   10                  15

Thr Val Thr Leu Thr Cys Arg Ser Ile Thr Gly Ala Val Thr Thr Ser
            20                  25                  30

Asn Tyr Ala Asn Trp Tyr Gln Gln Thr Pro Gly Gln Ala Pro Arg Gly
        35                  40                  45

Leu Ile Gly Gly Thr Asn Asn Arg Ala Pro Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Ala Leu Trp Tyr Ser Asn
                85                  90                  95

His Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 47
<211> LENGTH: 670
<212> TYPE: DNA
<213> ORGANISM: Artificial

<220> FEATURE:
<223> OTHER INFORMATION: Humanized light chain nucleic acid sequence

<400> SEQUENCE: 47
cagacagtgg tgacccagga gcctagcttc tccgtgtctc caggaggaac cgtgacactg        60
acctgcaggt ctatcacagg cgccgtgacc acaagcaact acgccaattg gtatcagcag       120
acaccaggac aggcaccaag gggactgatc ggaggaacca acaatagggc accaggagtg       180
cctgaccggt tcagcggatc catcctggga aacaaggccg ccctgacaat caccggagca       240
caggcagacg atgagtccga ttacttctgt gccctgtggt attctaatca ctgggtgttt       300
ggcggcggca caaagctgac cgtgctgggg cagcccaagg ccgctcctag cgtgacactg       360 tttcccccctt cctccgagga gctgcaggcc aacaaggcca ccctggtgtg cctgatctcc       420
gacttctatc ctggcgccgt gacagtggcc tggaaggctg attctagccc agtgaaggct       480
ggcgtggaga ccacaacccc ctccaagcag tctaacaata gtatgccgc ttcctcttac       540 ctgagcctga caccagagca gtggaagtcc caccggtctt acagctgcca ggtcactcac       600
gaaggctcta ccgtggaaaa gacagtcgca cccaccgaat gctcatgata agcttaaggg       660
ttcgatccct                                                              670

<210> SEQ ID NO 48
<211> LENGTH: 107
<212> TYPE: PRT
<213> ORGANISM: Homo sapiens

<400> SEQUENCE: 48

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 49
<211> LENGTH: 106
<212> TYPE: PRT
<213> ORGANISM: Homo sapiens

<400> SEQUENCE: 49

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys

```
65                   70                   75                   80

Ser His Arg Ser Tyr Ser Cys Gln Val Thr His Glu Gly Ser Thr Val
                85                   90                   95

Glu Lys Thr Val Ala Pro Thr Glu Cys Ser
            100                 105

<210> SEQ ID NO 50
<211> LENGTH: 330
<212> TYPE: PRT
<213> ORGANISM: Homo sapiens

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

ANTIBODIES WHICH BIND HUMAN ENDOTHELIN RECEPTOR A (ET$_A$R)

RELATED PATENT APPLICATIONS

This application is a U.S. National Stage Application pursuant to 35 U.S.C. § 371 of PCT/US2021/033088, filed May 19, 2021, which claims benefit of U.S. Provisional Application No. 63/027,465, filed on May 20, 2020, each incorporated in its entirety by reference herein.

TECHNICAL FIELD

Endothelin (ET) is a 21 amino acid vasoconstriction peptide hormone, important to the homeostasis and regulation of the biological functions of the cardiovascular system. ET is found not only in the endothelium but also in many other tissues and cell types (Barton et al., 2008, Can. J. Physiol. Pharmacol. 86:485-498). ET has three isoforms: ET-1, ET-2 and ET-3 which differ by a few amino acid residues and are all expressed in the human kidney. ET-1 and ET-2 bind to the two basic types of ET receptors: ET$_A$R and ET$_B$R. Both of these receptors are coupled to a Gq-protein and the formation of IP$_3$. Increased IP$_3$ causes calcium release by the sarcoplasmic reticulum, which causes smooth muscle contraction. In blood vessels, the ET$_A$R is dominant under normal conditions in terms of ET-1 effects on contraction. ET$_A$R has 63% sequence similarity with the human ET$_B$R. The endothelin axis and its receptors are implied in several physiopathological functions and dysfunctions. By way of non-limiting examples, arterial hypertension, atherosclerosis, coronary artery diseases, liver dysfunctions, cerebrovascular diseases, Crohn's disease, pulmonary fibrosis, asthma, etc. can be mentioned (R. Shah, Eur. J. Int. Med., 18:272-282, 2007). The two receptor subtypes exhibit contrasting cardiovascular actions under normal physiologic conditions. Moreover, endothelin receptors also turned out to be associated with the development of many cancers, by promoting proliferation, survival and dissemination of cancer cells as well as angiogenesis (Bagnato & Rosano, Int. J. of Biochem. & Cell Biology, 40:1443-1451, 2008).

ET-1 is the predominant isoform and ET-1 formation and release are stimulated by angiotensin II (AII), antidiuretic hormone (ADH), thrombin, cytokines, reactive oxygen species, and shearing forces acting on the vascular endothelium. ET-1 release is inhibited by prostacyclin and atrial natriuretic peptide as well as by nitric oxide. Once ET-1 is released by the endothelial cell, it binds to receptors on the target tissue (e.g., adjacent vascular smooth muscle). On release from the endothelium, the peptide causes vasoconstriction, mainly via ET$_A$R. Because of its powerful vasoconstrictor properties, and its effects on intracellular calcium, ET-1 has been implicated in the pathogenesis of hypertension, coronary vasospasm, and heart failure. In the latter condition, ET-1 is released by the failing myocardium where it can contribute to calcium overload and hypertrophy. Endothelin receptor antagonists have been shown to decrease mortality and improve hemodynamics in experimental models of heart failure.

Overproduction of ET-1 in pathophysiological conditions from the endothelium and other cellular sources can lead to constriction of vessels in conditions such as pulmonary hypertension (PAH), leading to vascular remodeling. This is exacerbated particularly where there is reduced production of opposing vasodilators such as nitric oxide, prostacyclin, and endothelium derived hyperpolarizing factor. Activation of the ET$_A$R can drive proliferation in multiple cell types and contributes to fibrosis and inflammation. Thus, ET$_A$R antagonists have been explored in the treatment of a range of cardio-pulmonary disorders, including portopulmonary hypertension, hypoplastic left heart syndrome, inoperable chronic thromboembolic pulmonary hypertension, PAH associated with systemic sclerosis, and exercise induced PAH (clinical trials.gov). A non-selective ET-1 receptor antagonist (bosentan) is currently used in the treatment of pulmonary hypertension. PAH is an often fatal disease with a dismal prognosis due to the lack of effective curative therapies.

ET-1 and ET$_A$R are also involved in other pathophysiological conditions. The experimental evidence collected to date indicates that the ET-1 system is activated in the presence of obesity, type 2 diabetes (T2DM) and metabolic syndrome (METs) defined as elevated blood pressure, abnormal fasting blood glucose and atherogenic dyslipidemia. This phenomenon results predominantly in an increased ET$_A$R-dependent vasoconstrictor tone and is associated with impaired NO bioactivity, hence leading to abnormal vascular function in patients with these conditions (Campia et al., Br J PharmacoL, 165:561-73, 2012; Cardillo et al., Circulation, 106:1783-7, 2002). Considerable evidence supports a mechanistic role of ET-1 in the pathophysiology of adiposity-related vascular dysfunction. Targeting the ET$_A$R, therefore, might have the potential for effective cardiovascular prevention in obesity, the MetS, and T2DM. ET$_A$R antagonists in clinical studies has shown promise in patients with type 2 diabetic nephropathy as Atrasentan reduced albuminuria and improved BP and lipid spectrum with manageable fluid overload-related adverse events in patients with type 2 diabetic nephropathy receiving g renin-angiotensin system (RAS) inhibitors (de Zeeuv et al., J Am Soc Nephrol, 25:1083-1093, 2014).

DISCLOSURE OF THE INVENTION

In accordance with the present invention, there are provided isolated antibodies, and antigen-binding fragments thereof, that specifically bind endothelin A receptor (ET$_A$R). These ET$_A$R antibodies, or antigen-binding fragments thereof, have a high affinity for ET$_A$R, function to effectively block ET-1 binding to ET$_A$R, are less immunogenic compared to their unmodified parent antibodies in a given species (e.g., in a human), and can be used to treat ET$_A$R-associated disorders. Importantly, compared to small molecule ET$_A$R antagonists, the antibodies of the present invention have advantages of longer serum half-life, higher target specificity, thereby limiting the risk of off-target toxicity and improving therapeutic window.

In various embodiments, the antibody or antigen-binding fragment is selected from a human antibody, a humanized antibody, chimeric antibody, a monoclonal antibody, a polyclonal antibody, a recombinant antibody, a single chain antibody, a diabody, a triabody, a tetrabody, a Fab fragment, a Fab' fragment, a Fab$_2$ fragment, a F(ab)'$_2$ fragment, a domain antibody, an IgD antibody, an IgE antibody, an IgM antibody, an IgG1 antibody, an IgG2 antibody, an IgG3 antibody, an IgG4 antibody, or an IgG4 antibody having at least one mutation in the hinge region that alleviates a tendency to form intra H-chain disulfide bonds. In various embodiments, the antibody is a chimeric antibody. In various embodiments, the antibody is a humanized antibody. In various embodiments, the antibody is a fully human antibody. In various embodiments, isolated antibodies, and antigen-binding fragments thereof, that have a high affinity for the human ET$_A$R of SEQ ID NO: 1 are provided.

In various embodiments, the antibody or antigen-binding fragment binds to $ET_AR$ protein with a dissociation constant $(K_D)$ of at least about $1\times10^{-6}$ M, at least about $1\times10^{-7}$ M, at least about $1\times10^{-8}$ M, at least about $1\times10^{-9}$ M, at least about $1\times10^{-10}$M, at least about $1\times10^{-11}$ M, or at least about $1\times10^{-11}$ M.

In various embodiments, an isolated antibody or antigen-binding fragment thereof of the present invention binds to human $ET_AR$ and comprises either: (a) a light chain CDR3 sequence identical, substantially identical or substantially similar to a CDR3 sequence selected from SEQ ID NOs: 16-18; (b) a heavy chain CDR3 sequence identical, substantially identical or substantially similar to a CDR3 sequence selected from SEQ ID NOs: 8-10; or (c) the light chain CDR3 sequence of (a) and the heavy chain CDR3 sequence of (b).

In various embodiments, the isolated antibody or antigen-binding fragment further comprises an amino acid sequence selected from: (d) a light chain CDR1 sequence identical, substantially identical or substantially similar to a CDR1 sequence selected from SEQ ID NOs: 11-13; (e) a light chain CDR2 sequence identical, substantially identical or substantially similar to a CDR2 sequence selected from SEQ ID NOs: 14-15; (f) a heavy chain CDR1 sequence identical, substantially identical or substantially similar to a CDR1 sequence selected from SEQ ID NOS: 2-4; (g) a heavy chain CDR2 sequence identical, substantially identical or substantially similar to a CDR2 sequence selected from SEQ ID NOs: 5-7; (h) the light chain CDR1 sequence of (d) and the heavy chain CDR1 sequence of (f); or (i) the light chain CDR2 sequence of (e) and the heavy chain CDR2 sequence of (g).

In various embodiments, the isolated human monoclonal antibody or antigen-binding fragment thereof of the present invention binds to human $ET_AR$ and comprises: (a) a light chain CDR1 sequence identical, substantially identical or substantially similar to a CDR1 sequence selected from SEQ ID NOs: 11-13; (b) a light chain CDR2 sequence identical, substantially identical or substantially similar to a CDR2 sequence selected from SEQ ID NOs: 14-15; (c) a light chain CDR3 sequence identical, substantially identical or substantially similar to a CDR3 sequence selected from SEQ ID NOs: 16-18; (d) a heavy chain CDR1 sequence identical, substantially identical or substantially similar to a CDR1 sequence selected from SEQ ID NOS: 2-4; (e) a heavy chain CDR2 sequence identical, substantially identical or substantially similar to a CDR2 sequence selected from SEQ ID NOs: 5-7; and (f) a heavy chain CDR3 sequence identical, substantially identical or substantially similar to a CDR3 sequence selected from SEQ ID NOs: 8-10.

In various embodiments, the isolated human monoclonal antibody or antigen-binding fragment thereof of the present invention binds to human $ET_AR$ and comprises: (a) a light chain CDR1 sequence identical, substantially identical or substantially similar to SEQ ID NO: 11; (b) a light chain CDR2 sequence identical, substantially identical or substantially similar to SEQ ID NO: 14; (c) a light chain CDR3 sequence identical, substantially identical or substantially similar to SEQ ID NO: 16; (d) a heavy chain CDR1 sequence identical, substantially identical or substantially similar to SEQ ID NO: 2; (e) a heavy chain CDR2 sequence identical, substantially identical or substantially similar to SEQ ID NO: 5; and (f) a heavy chain CDR3 sequence identical, substantially identical or substantially similar to SEQ ID NO: 8.

In various embodiments, the isolated human monoclonal antibody or antigen-binding fragment thereof of the present invention binds to human $ET_AR$ and comprises: (a) a light chain CDR1 sequence identical, substantially identical or substantially similar to SEQ ID NO: 12; (b) a light chain CDR2 sequence identical, substantially identical or substantially similar to SEQ ID NO: 14; (c) a light chain CDR3 sequence identical, substantially identical or substantially similar to SEQ ID NO: 17; (d) a heavy chain CDR1 sequence identical, substantially identical or substantially similar to SEQ ID NO: 3; (e) a heavy chain CDR2 sequence identical, substantially identical or substantially similar to SEQ ID NO: 6; and (f) a heavy chain CDR3 sequence identical, substantially identical or substantially similar to SEQ ID NO: 9.

In various embodiments, the isolated human monoclonal antibody or antigen-binding fragment thereof of the present invention binds to human $ET_AR$ and comprises: (a) a light chain CDR1 sequence identical, substantially identical or substantially similar to SEQ ID NO: 13; (b) a light chain CDR2 sequence identical, substantially identical or substantially similar to SEQ ID NO: 15; (c) a light chain CDR3 sequence identical, substantially identical or substantially similar to SEQ ID NO: 18; (d) a heavy chain CDR1 sequence identical, substantially identical or substantially similar to SEQ ID NO: 4; (e) a heavy chain CDR2 sequence identical, substantially identical or substantially similar to SEQ ID NO: 7; and (f) a heavy chain CDR3 sequence identical, substantially identical or substantially similar to SEQ ID NO: 10.

In various embodiments, an isolated antibody or antigen-binding fragment thereof of the present invention binds to human $ET_AR$ and comprises either: (a) a heavy and/or light chain variable domain(s), the variable domain(s) having a set of three light chain CDR1, CDR2, and CDR3 identical, substantially identical or substantially similar to SEQ ID NOs: 11-13, 14-15, and 16-18, and/or a set of three heavy chain CDR1, CDR2, and CDR3 identical, substantially identical or substantially similar to SEQ ID NOS: 2-4, 5-7, and 8-10; and (b) a set of four variable region framework regions from a human immunoglobulin (IgG). In various embodiments, the antibody can optionally include a hinge region. In various embodiments, the framework regions are chosen from human germline exon $X_H$, $J_H$, $V_K$ and $J_K$ sequences. In various embodiments, the antibody is a fully humanized antibody. In various embodiments, the antibody is a fully human antibody.

In various embodiments, an isolated antibody or antigen-binding fragment thereof of the present invention binds to human $ET_AR$ and comprises the heavy chain variable region having the amino acid sequence set forth in SEQ ID NO: 19 and the light chain variable region having the amino acid sequence set forth in SEQ ID NO: 21. In various embodiments, an isolated antibody or antigen-binding fragment thereof of the present invention binds to human $ET_AR$ and comprises the heavy chain variable region having the amino acid sequence set forth in SEQ ID NO: 23 and the light chain variable region having the amino acid sequence set forth in SEQ ID NO: 25. In various embodiments, an isolated antibody or antigen-binding fragment thereof of the present invention binds to human $ET_AR$ and comprises the heavy chain variable region having the amino acid sequence set forth in SEQ ID NO: 27 and the light chain variable region having the amino acid sequence set forth in SEQ ID NO: 29.

In various embodiments, the isolated antibody or antigen-binding fragment, when bound to human $ET_AR$: (a) binds to human $ET_AR$ with substantially the same or greater Kd as a reference antibody; (b) competes for binding to human $ET_AR$ with said reference antibody; or (c) is less immunogenic in a human subject than said reference antibody, wherein said reference antibody comprises a combination of heavy chain variable domain and light chain variable domain sequences selected from SEQ ID NOs: 19/23/27 and 21/25/29, respectively.

In various embodiments, an isolated humanized antibody or antigen-binding fragment thereof of the present invention binds to human ET$_A$R and comprises a heavy chain variable region having a sequence identical, substantially identical or substantially similar to SEQ ID NOs: 33-35, and a light chain variable region having the sequence identical, substantially identical or substantially similar to SEQ ID NOs: 36-37.

In various embodiments, the isolated antibody or antigen-binding fragment, when bound to human ET$_A$R: (a) binds to human ET$_A$R with substantially the same or greater Kd as a reference antibody; (b) competes for binding to human ET$_A$R with said reference antibody; or (c) is less immunogenic in a human subject than said reference antibody, wherein said reference antibody comprises the combination of heavy chain variable domain and light chain variable domain sequences set forth in SEQ ID NOs: 27 and 29.

In various embodiments, an isolated humanized antibody or antigen-binding fragment thereof of the present invention binds to human ET$_A$R and comprises a heavy chain having a sequence identical, substantially identical or substantially similar to SEQ ID NOs: 38, 42 and 44, and a light chain variable region having the sequence identical, substantially identical or substantially similar to SEQ ID NOs: 40 and 46. In various embodiments, an isolated humanized antibody or antigen-binding fragment thereof of the present invention binds to human ET$_A$R and comprises the heavy chain sequence set forth in SEQ ID NO: 38, and the light chain sequence set forth in SEQ ID NO: 40. In various embodiments, an isolated humanized antibody or antigen-binding fragment thereof of the present invention binds to human ET$_A$R and comprises the heavy chain sequence set forth in SEQ ID NO: 42, and the light chain sequence set forth in SEQ ID NO: 40. In various embodiments, an isolated humanized antibody or antigen-binding fragment thereof of the present invention binds to human ET$_A$R and comprises the heavy chain sequence set forth in SEQ ID NO: 44, and the light chain sequence set forth in SEQ ID NO: 40.

In another aspect, the present invention relates to a pharmaceutical composition comprising an isolated antibody or antigen-binding fragment of the present invention in admixture with a pharmaceutically acceptable carrier. In various embodiments, the pharmaceutical composition comprises an isolated human antibody in admixture with a pharmaceutically acceptable carrier. In various embodiments, the pharmaceutical composition is formulated for administration via a route selected from the group consisting of subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or via infusions.

In another aspect, the present invention relates to methods of treating a subject suffering from a ET$_A$R-associated disorder, comprising administering to said subject a therapeutically effective amount (either as monotherapy or in a combination therapy regimen) of an antibody or antigen-binding fragment thereof of the present invention. In various embodiments, the subject is a human subject.

In various embodiments, the ET$_A$R-associated disorder is a metabolic disorder selected from the group consisting of diabetes, diabetic myopathy, diabetic nephropathy, diabetic neuropathy, diabetic retinopathy, obesity, dyslipidemia, sarcopenic obesity, fatty liver disease (e.g., nonalcoholic fatty liver disease (NAFLD); nonalcoholic steatohepatitis (NASH)), insulin resistance, and hemochromatosis.

In various embodiments, the ET$_A$R-associated disorder is a cardiovascular disease selected from the group consisting of angina, heart attack (myocardial infarction), atherosclerosis, heart failure, cardiovascular disease, rheumatic heart disease, cardiac arrhythmias (abnormal heart rhythms), cerebrovascular disease, congenital heart defects, cardiomyopathy, left ventricular hypertrophy, right ventricular hypertrophy, post-infarction heart rupture, infections of the heart, coronary artery disease, peripheral arterial disease, renal artery stenosis, aortic aneurysm, myocardial diseases, heart valve disorders, myocarditis, pericarditis, and pulmonary arterial hypertension (PAH).

In another aspect, the present invention provides combination therapies designed to treat a metabolic disorder in a subject, comprising (a) administering to said subject a therapeutically effective amount of an antibody or antigen-binding fragment thereof of the present invention, and (b) administering a glucose-lowering agent. In various embodiments, the glucose-lowering agent is selected from anti-diabetic agents, anti-hyperglycemic agents, lipid lowering agents, anti-hypertensive agents, and anti-obesity agents. In various embodiments, the glucose-lowering agent is selected from biguanides, sulfonylureas, meglitinides, thiazolidinediones (TZDs), α-glucosidase inhibitors, DPP-4 inhibitors, bile acid sequestrants, dopamine-2 agonists, SGLT2 inhibitors, GLP-1R agonists, amylin mimetics, and insulins.

In another aspect, the present invention provides combination therapies designed to treat a cardiovascular disease in a subject, comprising (a) administering to said subject a therapeutically effective amount of an isolated antibody or antigen-binding fragment of the present invention, and (b) administering a second agent selected from the group consisting of antihypertensive agents, agents for treating chronic heart failure, atherosclerosis or related diseases.

In another aspect, an isolated immunoconjugate or fusion protein comprising an antibody or antigen-binding fragment conjugated to, linked to (or otherwise stably associated with) an effector molecule is provided. In various embodiments, the effector molecule is an immunotoxin, cytokine, chemokine, therapeutic agent, or chemotherapeutic agent.

In another aspect, the antibodies or antigen-binding fragments disclosed herein may be covalently linked to (or otherwise stably associated with) an additional functional moiety, such as a label or a moiety that confers desirable pharmacokinetic properties. In various embodiments, the label is selected from the group consisting of: a fluorescent label, a radioactive label, and a label having a distinctive nuclear magnetic resonance signature.

In another aspect, the present invention provides a method for detecting in vitro or in vivo the presence of human ET$_A$R peptide in a sample, e.g., for diagnosing a human ET$_A$R-associated disorder.

In another aspect, isolated nucleic acids comprising the polynucleotide sequence that encodes the antibodies or antigen-binding fragments disclosed herein are provided. In various embodiments, the polynucleotide comprises a heavy chain sequences as set forth in SEQ ID NOs: 38, 42 and 44 a light chain sequence as set forth in SEQ ID NOs: 40 and 46, or both. Also provided are expression vectors comprising the nucleic acid of the present invention. Also provided are isolated cells comprising the expression vectors of the invention. In various embodiments, the cell is a host cell comprising an expression vector of the present invention. In various embodiments, the cell is a hybridoma, wherein the chromosome of the cell comprises a nucleic acid of the present invention. Further provided is a method of making the antibody or antigen-binding fragment of the present invention comprising culturing or incubating the cell under conditions that allow the cell to express the antibody or antigen-binding fragment of the present invention.

MODE(S) OF CARRYING OUT THE INVENTION

Figure 1:
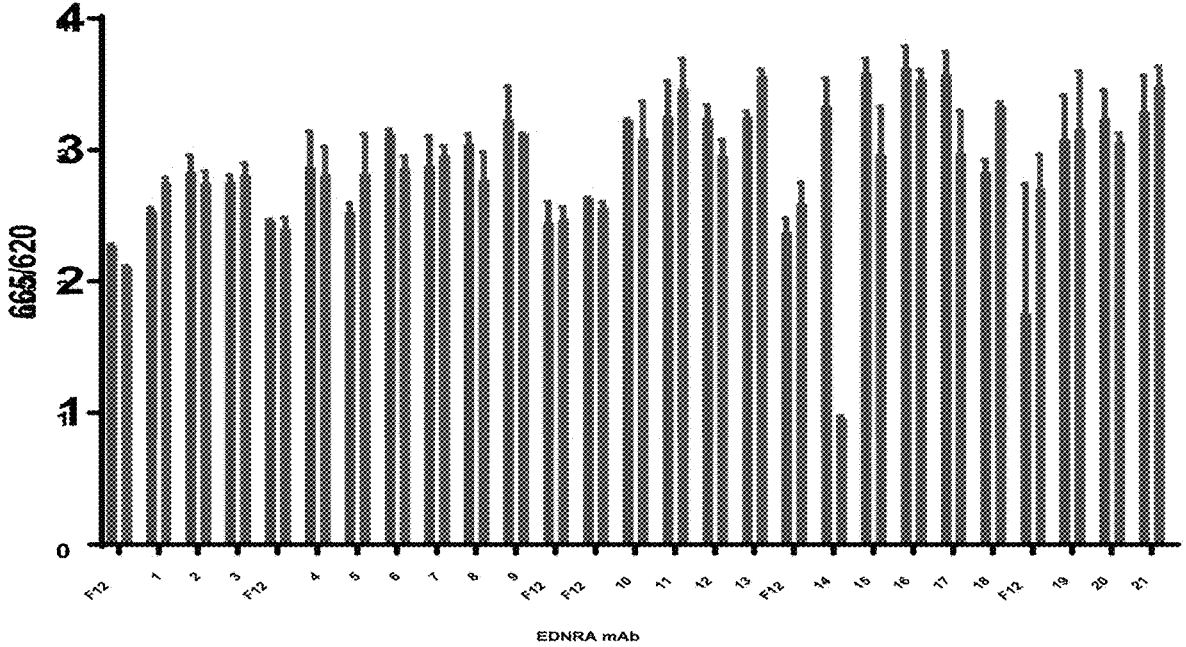
FIG. 1 is a bar graph depicting the $ET_AR$ functional assay data for murine mAbs #1-#21.

The present invention relates to antigen binding proteins such as antibodies, or antigen-binding fragments thereof that specifically bind to human $ET_AR$. In one aspect, there are provided isolated antibodies, and antigen-binding fragments thereof, that specifically bind $ET_AR$, have a high affinity for $ET_AR$, function to inhibit $ET_AR$, are less immunogenic compared to their unmodified parent antibodies in a given species (e.g., a human), and can be used to treat human disorders mediated by $ET_AR$. Also provided are nucleic acid molecules, and derivatives and fragments thereof, comprising a sequence of polynucleotides that encode all or a portion of a polypeptide that binds to $ET_AR$, such as a nucleic acid encoding all or part of an anti-$ET_AR$ antibody, antibody fragment, or antibody derivative. Also provided are vectors and plasmids comprising such nucleic acids, and cells or cell lines comprising such nucleic acids and/or vectors and plasmids. Also provided are methods of making, identifying, or isolating antigen binding proteins that bind to human $ET_AR$, such as anti-$ET_AR$ antibodies, methods of determining whether an antigen binding protein binds to $ET_AR$, methods of making compositions, such as pharmaceutical compositions, comprising an antigen binding protein that binds to human $ET_AR$, and methods for administering an antibody, or antigen-binding fragment thereof that binds $ET_AR$ to a subject, for example, methods for treating a condition mediated by $ET_AR$.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present invention are generally performed according to conventional methods well known in the art and as described in various general and more specific references that are cited and discussed throughout the present specification unless otherwise indicated. See, e.g., Green and Sambrook, Molecular Cloning: A Laboratory Manual, 4th ed., Cold Spring Harbor Laboratory Press, Cold Spring Harbor, N.Y. (2012), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of subjects.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 80 to 119, or by the actual residue at that site such as Ser80 to Ser119. A particular polypeptide or polynucleotide sequence also can be described based upon how it differs from a reference sequence. Polynucleotide and polypeptide sequences of particular light and heavy chain variable domains are designated L1 ("light chain variable domain 1") and H1 ("heavy chain variable domain 1"). Antibodies comprising a light chain and heavy chain are indicated by combining the name of the light chain and the name of the heavy chain variable domains. For example, "L4H7," indicates, for example, an antibody comprising the light chain variable domain of L4 and the heavy chain variable domain of H7.

The term "antibody" is used herein to refer to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

In a full-length antibody, each heavy chain is comprised of a heavy chain variable region (abbreviated herein as HCVR or VH) and a heavy chain constant region. The heavy chain constant region is comprised of three domains, CH1, CH2 and CH3 (and in some instances, CH4). Each light chain is comprised of a light chain variable region (abbreviated herein as LCVR or VL) and a light chain constant region. The light chain constant region is comprised of one domain, $C_L$. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The extent of the framework region and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The CDRs are primarily responsible for binding to an epitope of an antigen. The CDRs of each chain are typically referred to as CDR1, CDR2, CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The Kabat definition is a standard for numbering the residues in an antibody and is typically used to identify CDR regions. The Kabat database is now maintained online and CDR sequences can be determined, for example, see IMGT/V-QUEST programme version: 3.2.18 Mar. 29, 2011, available on the internet and Brochet, X. et al., Nucl. Acids Res. 36, W503-508, 2008). The Chothia definition is similar to the Kabat definition, but the Chothia definition takes into account positions of certain structural loop regions. See, e.g., Chothia et al., J. Mol. Biol., 196: 901-17, 1986; Chothia et al., Nature, 342: 877-83, 1989. The AbM definition uses an integrated suite of computer programs produced by Oxford Molecular Group that model antibody structure. See, e.g., Martin et al., Proc. Natl. Acad. Sci. USA, 86:9268-9272, 1989; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198, 1999. The contact definition is based on an analysis of the available complex crystal structures. See, e.g., MacCallum et al., J. Mol. Biol., 5:732-45, 1996.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

Antibodies exist as intact immunoglobulins or as a number of well characterized fragments. Such fragments include Fab fragments, Fab' fragments, $Fab_2$, $F(ab)'_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), intrabodies, and epitope-binding fragments or antigen binding fragments of any of the above.

Papain digestion of antibodies produces two identical antigen-binding fragments, called "Fab" fragments, each with a single antigen-binding site. A "Fab fragment" comprises one light chain and the CH1 and variable regions of one heavy chain. The heavy chain of a Fab molecule cannot form a disulfide bond with another heavy chain molecule. A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an $F(ab')_2$ molecule.

Pepsin treatment of an antibody yields an $F(ab')_2$ fragment that has two antigen-combining sites and is still capable of cross-linking antigen. A "$F(ab')_2$ fragment" contains two light chains and two heavy chains containing a portion of the constant region between the CH1 and CH2 domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649, U.S. Pat. Nos. 4,946,778 and 5,260,203, the disclosures of which are incorporated by reference.

The terms "an antigen-binding fragment" and "antigen-binding protein" as used herein means any protein that binds a specified target antigen. "Antigen-binding fragment" includes but is not limited to antibodies and binding parts thereof, such as immunologically functional fragments. An exemplary antigen-binding fragment of an antibody is the heavy chain and/or light chain CDR(s), or the heavy and/or light chain variable region.

The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. In one aspect, such a fragment will retain at least one CDR present in the full-length light or heavy chain, and in some embodiments will comprise a single heavy chain and/or light chain or portion thereof. These biologically active fragments can be produced by recombinant DNA techniques or can be produced by enzymatic or chemical cleavage of antigen binding proteins, including intact antibodies. Immunologically functional immunoglobulin fragments include, but are not limited to, Fab, a diabody, Fab', F(ab')$_2$, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

Diabodies are bivalent antibodies comprising two polypeptide chains, wherein each polypeptide chain comprises VH and VL regions joined by a linker that is too short to allow for pairing between two regions on the same chain, thus allowing each region to pair with a complementary region on another polypeptide chain (see, e.g., Holliger et al., Proc. Natl. Acad. Sci. USA, 90:6444-48, 1993; and Poljak et al., Structure, 2:1121-23, 1994). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al., Proc. Natl. Acad. Sci. USA, 78:5807, 1981; by "polydoma" techniques (see, e.g., U.S. Pat. No. 4,474,893); or by recombinant DNA techniques. In various embodiments bispecific antibodies of the present disclosure can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method.

The term "chimeric antibody" as used herein refers to an antibody which has framework residues from one species, such as human, and CDRs (which generally confer antigen binding) from another species, such as a murine antibody that specifically binds targeted antigen.

The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "humanized antibody" as used herein refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. In various embodiments, the framework regions are chosen from human germline exon $X_H$, $J_H$, $V_K$ and $J_K$ sequences. For example, acceptor sequences for humanization of FR of a $V_H$ domain can be chosen from genuine $V_H$ exons $V_H$ 1-18 (Matsuda et al., Nature Genetics 3:88-94, 1993) or $V_H$1-2 (Shin et al., EMBO J. 10:3641-3645, 1991) and for the hinge region ($J_H$), exon $J_H$-6 (Mattila et al., Eur. J. Immunol. 25:2578-2582, 1995). In other examples, germline $V_K$ exon B3 (Cox et al., Eur. J. Immunol. 24:827-836, 1994) and $J_K$ exon $J_K$-1 (Hieter et al., J. Biol. Chem. 257:1516-1522, 1982) can be chosen as acceptor sequences for $V_L$ domain humanization.

The term "recombinant human antibody", as used herein, is intended to include all human antibodies that are prepared, expressed, created or isolated by recombinant means, such as antibodies expressed using a recombinant expression vector transfected into a host cell; antibodies isolated from a recombinant, combinatorial human antibody library; antibodies isolated from an animal (e.g., a mouse) that is transgenic for human immunoglobulin genes; or antibodies prepared, expressed, created or isolated by any other means that involves splicing of human immunoglobulin gene sequences to other DNA sequences. Such recombinant human antibodies have variable and constant regions derived from human germline immunoglobulin sequences. In various embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. All such recombinant means are well known to those of ordinary skill in the art.

The term "anti-ETR antagonist antibody" (interchangeably termed "anti-ETR antibody") refers to an antibody that is able to bind to ETR and inhibit ETR biological activity and/or downstream pathway(s) mediated by ETR signaling. An anti-ETR antagonist antibody encompasses antibodies that block, antagonize, suppress or reduce (including significantly) ETR biological activity, including downstream pathways mediated by ETR signaling, such as receptor binding and/or elicitation of a cellular response to ETR. For purpose of the present invention, it will be explicitly understood that the term "anti-ETR antagonist antibody" encompasses all the previously identified terms, titles, and functional states and characteristics whereby the ETR itself, an ETR biological activity (including but not limited to its ability to mediate any aspect of headache), or the consequences of the biological activity, are substantially nullified, decreased, or neutralized in any meaningful degree. In some embodiment, an anti-ETR antagonist antibody binds ETR and prevents ETR binding to a ETR receptor. In other embodiments, an anti-ETR antibody binds ETR and prevents activation of a ETR receptor. Examples of anti-ETR antagonist antibodies are provided herein.

The term "epitope" as used herein includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present disclosure. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen.

An antigen binding protein, including an antibody, "specifically binds" to an antigen if it binds to the antigen with a high binding affinity as determined by a dissociation constant ($K_D$, or corresponding Kb, as defined below) value of at least $1\times10^{-6}$ M, or at least $1\times10^{-7}$ M, or at least $1\times10^{-8}$ M, or at least $1\times10^{-9}$ M, or at least $1\times10^{-10}$ M, or at least $1\times10^{-11}$ M. An antigen binding protein that specifically binds to the human antigen of interest may be able to bind to the same antigen of interest from other species as well, with the same or different affinities. The term "$K_D$" as used herein refers to the equilibrium dissociation constant of a particular antibody-antigen interaction.

The term "surface plasmon resonance" as used herein refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., Ann. Biol. Clin., 51:19-26, 1993; Jonsson U. et al., Biotechniques, 11:620-627, 1991; Jonsson B. et al., J. Mol. Recognit., 8:125-131, 1995; and Johnsson B. et al., Anal. Biochem, 198:268-277, 1991.

The term "immunogenicity" as used herein refers to the ability of an antibody or antigen binding fragment to elicit an immune response (humoral or cellular) when administered to a recipient and includes, for example, the human anti-mouse antibody (HAMA) response. A HAMA response is initiated when T-cells from a subject make an immune response to the administered antibody. The T-cells then recruit B-cells to generate specific "anti-antibody" antibodies.

The term "immune cell" as used herein means any cell of hematopoietic lineage involved in regulating an immune response against an antigen (e.g., an autoantigen). In various embodiments, an immune cell is, e.g., a T cell, a B cell, a dendritic cell, a monocyte, a natural killer cell, a macrophage, Langerhan's cells, or Kuffer cells.

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "recombinant polypeptide", as used herein, is intended to include all polypeptides, including fusion molecules that are prepared, expressed, created, derived from, or isolated by recombinant means, such as polypeptides expressed using a recombinant expression vector transfected into a host cell.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)

Isoleucine (I), Leucine (L), Methionine (M), and Valine (V)

Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within +2 is included. In various embodiments, those that are within +1 are included, and in various embodiments, those within +0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included. Exemplary amino acid substitutions are set forth in Table 1.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | |
| Glu | Asp | |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |

TABLE 1-continued

| Original Residues | Exemplary Substitutions | Preferred Substitutions |
|---|---|---|
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 25:3389-3402, 1997. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The terms "substantial similarity" or "substantially similar," in the context of polypeptide sequences, indicate that a polypeptide region has a sequence with at least 70%, typically at least 80%, more typically at least 85%, or at least 90% or at least 95% sequence similarity to a reference sequence. For example, a polypeptide is substantially similar to a second polypeptide, for example, where the two peptides differ by one or more conservative substitution(s).

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "immunoconjugate" or "fusion protein" as used herein refers to a molecule comprising an antibody or antigen-binding fragment thereof conjugated (or linked) directly or indirectly to an effector molecule. The effector molecule can be a detectable label, an immunotoxin, cytokine, chemokine, therapeutic agent, or chemotherapeutic agent. The antibody or antigen-binding fragment thereof may be conjugated to an effector molecule via a peptide linker. An immunoconjugate and/or fusion protein retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate may also be referred to as an antibody drug conjugate (ADC). Because immunoconjugates and/or fusion proteins are originally prepared from two molecules with separate functionalities, such as an antibody and an effector molecule, they are also sometimes referred to as "chimeric molecules."

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. As used herein, "treatment" is an approach for obtaining beneficial or desired clinical results. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms.

It is understood that aspects and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

ET$_A$R

ET$_A$R is a member of class A of the GPCR family, comprises seven transmembrane domains. Its extracellular domain is very small, only ⅐ of the complete protein sequence. Human ET$_A$R has 63% sequence similarity with the human ET$_B$R. The two receptor subtypes exhibit contrasting cardiovascular actions under normal physiologic conditions. On release from the endothelium, the peptide causes vasoconstriction, mainly via ET$_A$R. The expression of ET$_A$R on endothelial and smooth muscle results in broad receptor distributions in tissues or organs receiving a blood supply. Highest relative expression of ET$_A$R mRNA is associated with the heart and lungs with relatively low expression in the CNS. ET$_A$R mRNA was the fifth most abundant GPCR in heart atria and 11th in ventricle, emphasizing the importance of the ET pathway in the cardiovascular system (Regard et al., 2008 Anatomical profiling of G protein coupled receptor expression. Cell 135:561-571).

The term "ET$_A$R" as used herein includes human ET$_A$R (hET$_A$R), variants, isoforms, and species homologs of hET$_A$R, and analogs having at least one common epitope with hET$_A$R. In various embodiments, a hET$_A$R as used herein may comprise the amino acid sequence set forth in SEQ ID NO: 1:

(SEQ ID NO: 1)

METLCLRASFWLALVGCVISDNPERYSTNLSNHVDD

FTTFRGTELSFLVTTHQPTNLVLPSNGSMHNYCPQ

QTKITSAFKYINTVISCTIFIVGMVGNATLLRIIY

QNKCMRNGPNALIASLALGDLIYVVIDLPINVFKL

LAGRWPFDHNDFGVFLCKLFPFLQKSSVGITVLNL

CALSVDRYRAVASWSRVQGIGIPLVTAIEIVSIWI

LSFILAIPEAIGFVMVPFEYRGEQHKTCMLNATSK

FMEFYQDVKDWWLFGFYFCMPLVCTAIFYTLMTCE

MLNRRNGSLRIALSEHLKQRREVAKTVFCLVVIFA

LCWFPLHLSRILKKTVYNEMDKNRCELLSFLLLMD

YIGINLATMNSCINPIALYFVSKKFKNCFQSCLCC

CCYQSKSLMTSVPMNGTSIQWKNHDQNNHNTDRSS

HKDSMN

In various embodiments, a ET$_A$R comprises an amino acid sequence that shares an observed homology of, e.g., at least 70%, at least 75%, at least 80%, at least 85%, at least 90%, at least 95%, at least 96%, at least 97%, at least 98%, or at least 99% with the human ET$_A$R sequence of SEQ ID NO: 1. In some embodiments, the has at least 70%, at least 75%, at least 80%, at least 85%, at least 90%, at least 95%, at least 96%, at least 97%, at least 98%, at least 99%, at least 1×, at least 1.5×, at least 2×, at least 2.5×, or at least 3× activity of the human ET$_A$R of SEQ ID NO: 1. Variants of ET$_A$R may be described herein by reference to the addition, deletion, or substitution of amino acid residue present at a given position in the 360 amino acid sequence of SEQ ID NO: 1. Thus, for example, the term "P29W" indicates that the "P" (proline, in standard single letter code) residue at position 29 in SEQ ID NO: 1 has been substituted with a "W" (tryptophan, in standard single letter code).

Antibodies

Methods of generating novel antibodies that bind to human ET$_A$R are known to those skilled in the art. For example, a method for generating a monoclonal antibody that binds specifically to an ET$_A$R may comprise administering to a mouse an amount of an immunogenic composition comprising the ET$_A$R effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the ET$_A$R. Once obtained, a hybridoma can be propagated in a cell culture, optionally in culture conditions where the hybridoma-derived cells produce the monoclonal antibody that binds specifically to ET$_A$R. The monoclonal antibody may be purified from the cell culture. A variety of different techniques are then available for testing antibody:antigen interactions to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. USA, 90: 2551-2555, 1993; Jakobovits et al., Nature, 362:255-258, 1993; Lonberg et al., U.S. Pat. No. 5,545,806; Surani et al., U.S. Pat. No. 5,545,807.

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548, 640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al., Science, 240:1041-1043, 1988; Liu et al., PNAS USA, 84:3439-3443, 1987; Liu et al., J. Immunol. 139:3521-3526, 1987; Sun et al., PNAS USA, 84:214-218, 1987; Nishimura et al., Canc. Res. 47:999-1005, 1987; Wood et al., Nature 314:446-449, 1985; and Shaw et al., J. Natl Cancer Inst., 80:1553-1559, 1988).

Methods for humanizing antibodies have been described in the art. In practice, humanized antibodies are typically human antibodies in which some hypervariable region residues and possibly some framework region residues are substituted by residues from analogous sites in rodent antibodies. Accordingly, such "humanized" antibodies are chimeric antibodies wherein substantially less than an intact human variable region has been substituted by the corresponding sequence from a nonhuman species. To a degree, this can be accomplished in connection with techniques of humanization and display techniques using appropriate libraries. It will be appreciated that murine antibodies or antibodies from other species can be humanized or primatized using techniques well known in the art (see e.g., Winter et al., Immunol Today, 14:43-46, 1993; and Wright et al., Crit. Reviews in Immunol., 12125-168, 1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777, 085). Also, the use of Ig cDNA for construction of chimeric immunoglobulin genes is known in the art (Liu et al., P.N.A.S. 84:3439, 1987; J. Immunol. 139:3521, 1987). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683, 202). Alternatively, a library is made and screened to isolate the sequence of interest. The DNA sequence encoding the variable region of the antibody is then fused to human constant region sequences. The sequences of human constant regions to genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. In various embodiments, the isotype is selected from the group consisting of IgG1, IgG2, IgG3 and IgG4. Either of the human light chain constant regions, kappa or lambda, may be used. The chimeric, humanized antibody is then expressed by conventional methods.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, the importance of particular framework amino acid residues is determined experimentally once a low-avidity humanized construct is obtained, by reversion of single residues to the mouse sequence and assaying antigen-binding as described by Riechmann et al, 1988. Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

The choice of human variable regions, both light and heavy, to be used in making the desired humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296, 1993; Chothia et al., J. Mol. Biol., 196:901, 1987). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. USA, 89:4285, 1992; Presta et al., J. Immunol., 151:2623, 1993).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an anti-ET$_A$R antibody or antigen-binding fragment thereof comprises the steps of synthesizing a library of human antibodies on phage, screening the library with ET$_A$R or an antibody-binding portion thereof, isolating phage that bind ET$_A$R, and obtaining the antibody from the phage. By way of another example, one method for preparing the library of antibodies for use in phage display techniques comprises the steps of immunizing a non-human animal comprising human immunoglobulin loci with ET$_A$R or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-$ET_AR$ antibodies of the invention may be obtained in this way.

Recombinant human anti-ETR antibodies of the invention can also be isolated by screening a recombinant combinatorial antibody library. Preferably the library is a scFv phage display library, generated using human VL and VH cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85, 1992; Huse et al., Science 246: 1275-1281, 1989; McCafferty et al., Nature 348:552-554, 1990; Griffiths et al., EMBO J. 12:725-734, 1993; Hawkins et al., J. Mol. Biol. 226:889-896, 1992; Clackson et al., Nature 352:624-628, 1991; Gram et al., Proc. Natl. Acad. Sci. USA 89:3576-3580, 1992; Garrad et al., Bio/Technology 9:1373-1377, 1991; Hoogenboom et al., Nuc. Acid Res. 19:4133-4137, 1991; and Barbas et al., Proc. Natl. Acad. Sci. USA 88:7978-7982, 1991, each incorporated herein by reference for purposes of teaching preparation and screening of phase display libraries.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics 7:13-21, 1994; and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, Xeno-Mouse™ mice further contain approximately all of the human lambda light chain locus. See Mendez et al., Nature Genetics 15:146-156, 1997, Green and Jakobovits, J. Exp. Med. 188:483-495 (1998), and WO 98/24893 (each incorporated by reference in its entirety for purposes of teaching the preparation of fully human antibodies). In another aspect, the present invention provides a method for making anti-$ET_AR$ antibodies from non-human, non-mouse animals by immunizing non-human transgenic animals that comprise human immunoglobulin loci with a $ET_AR$ antigen. One can produce such animals using the methods described in the above-cited documents.

Characterization of Antibody Binding to Antigen

Antibodies of the present invention can be tested for binding to human $ET_AR$ by, for example, standard ELISA. As an example, microtiter plates are coated with purified $ET_AR$ in PBS, and then blocked with 5% bovine serum albumin in PBS. Dilutions of antibody (e.g., dilutions of plasma from $ET_AR$-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml) and analyzed at OD of 405-650. Preferably, mice which develop the highest titers will be used for fusions. An ELISA assay can also be used to screen for hybridomas that show positive reactivity with $ET_AR$ immunogen. Hybridomas that bind with high avidity to $ET_AR$ are subcloned and further characterized. One clone from each hybridoma, which retains the reactivity of the parent cells (by ELISA), can be chosen for making a 5-10 vial cell bank stored at −140° C., and for antibody purification.

To determine if the selected anti-$ET_AR$ monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using $ET_AR$ coated-ELISA plates as described above. Biotinylated mAb binding can be detected with a strep-avidin-alkaline phosphatase probe. To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-$ET_AR$ human IgGs can be further tested for reactivity with ETR antigen by Western blotting. Briefly, $ET_AR$ can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Identification of Anti-$ET_AR$ Antibodies

The present invention provides monoclonal antibodies, and antigen-binding fragments thereof, that specifically bind to $ET_AR$ antigen.

Further included in the present invention are antibodies that bind to the same epitope as the anti-$ET_AR$ antibodies of the present invention. To determine if an antibody can compete for binding to the same epitope as the epitope bound by the anti-$ET_AR$ antibodies of the present invention, a cross-blocking assay, e.g., a competitive ELISA assay, can be performed. In an exemplary competitive ELISA assay, $ET_AR$ coated on the wells of a microtiter plate is pre-incubated with or without candidate competing antibody and then the biotin labeled anti-$ET_AR$ antibody of the invention is added. The amount of labeled anti-$ET_AR$ antibody bound to the ET$_A$R antigen in the wells is measured using avidin-peroxidase conjugate and appropriate substrate. The antibody can be labeled with a radioactive or fluorescent label or some other detectable and measurable label. The amount of labeled anti-ET$_A$R antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an anti-ET$_A$R antibody of the invention if the candidate antibody can block binding of the ET$_A$R antibody by at least 20%, preferably by at least 20-50%, even more preferably, by at least 50% as compared to the control performed in parallel in the absence of the candidate competing antibody. It will be understood that variations of this assay can be performed to arrive at the same quantitative value.

The amino acid sequences of the heavy chain variable region CDRs and the light chain variable region CDRs of three murine antibodies, 178D1F6C1G6 (also referred to hereinafter as "A1"), 336D8G9 (also referred to hereinafter as "A2") and 312A10E5 (also referred to hereinafter as "A3"), generated as described herein, are shown below in Table 2.

TABLE 2

| Heavy Chain CDRs | | | |
| --- | --- | --- | --- |
| Ab | HCDR1 | HCDR2 | HCDR3 |
| A1 | SYWMN (SEQ ID NO: 2) | QIYPGNG DTNYNGK FRG (SEQ ID NO: 5) | RGSLDY (SEQ ID NO: 8) |
| A2 | DYYIH (SEQ ID NO: 3) | RIDPEDGD TEYAPKF QG (SEQ ID NO: 6) | NWYSNSY (SEQ ID NO: 9) |
| A3 | GYTFTNYGMS (SEQ ID NO: 4) | WINTYSGE STYADDFK G (SEQ ID NO: 7) | SLNRDTWFTY (SEQ ID NO: 10) |

| Light Chain CDRs | | | |
| --- | --- | --- | --- |
| Ab | LCDR1 | LCDR2 | LCDR3 |
| A1 | KSSHSLVHS NGDTYLH (SEQ ID NO: 11) | KVSNRFS (SEQ ID NO: 14) | SQTTYVPYT (SEQ ID NO: 16) |
| A2 | RSSQSLVHS NGNTYLH (SEQ ID NO: 12) | KVSNRFS (SEQ ID NO: 14) | SQSTHVPYT (SEQ ID NO: 17) |
| A3 | RSITGAVT TSNYAN (SEQ ID NO: 13) | GTNNRAP (SEQ ID NO: 15) | ALWYSNHWV (SEQ ID NO: 18) |

In various embodiments of the present invention, the antibody or antigen-binding fragment is a murine antibody, 178D1F6C1G6 ("A1"), comprising the heavy chain variable region sequence of SEQ ID NO: 19:

```
                                   (SEQ ID NO: 19)
QVQLQQSGAELVRPGSSVRISCKAFDYAFSSYWMN

WVKQRPGQDLEWIGQIYPGNGDTNYNGKFRGKASL

TADKSSSTAYMHLSSLTSEDSAVYFCARRGSLDYW

GQGTSVTVSS
``` and the light chain variable region sequence of SEQ ID NO: 21:

```
                                   (SEQ ID NO: 21)
DVVMTQIPLSLPVSLGDQSSISCKSSHSLVHSNGD

TYLHWFLQKPGQSPKLLIYKVSNRFSGVPDRFTGS

GSGTEFTLKISRVEAEDLGVYFCSQTTYVPYTFGG

GTKLEIK
```

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 19, or its corresponding polynucleotide sequence SEQ ID NO: 20:

```
                                   (SEQ ID NO: 20)
caggttcagctgcagcagtctgggctgagttggt gaggcctgggtcctcagtgaggatttcctgcaagg cttttgactatgcattcagtagctactggatgaac tgggtgaagcagaggcctggacaggatcttgagtg gattggacagatttatcctggaaatggtgatacta actacaatggaaagttcaggggtaaagcctcactg actgcagacaaatcctccagcacagcctacatgca cctcagcagcctaacatctgaggactctgcggtct atttctgtgcaagacgggggtctttggactactgg ggtcaaggaacctcagtcaccgtctcctca
``` and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 21, or its corresponding polynucleotide sequence SEQ ID NO: 22:

```
                                   (SEQ ID NO: 22)
gatgtggtgatgacccaaattccactctccctgcc tgtcagtcttggagatcaatcctccatctcttgca aatctagtcatagccttgtacatagtaatggagac acctatttacattggttcctgcagaagccaggcca gtctccaaagctcctgatctacaaagtctccaacc
```

-continued

```
gattttctggggtcccagacaggttcactggcagt ggttcagggacagagttcacactcaagatcagcag agtggaggctgaggatctgggagtttatttctgct ctcaaactacatatgttccgtacacgttcggaggg gggaccaagctggaaataaaa
```

In various embodiments of the present invention, the antibody or antigen-binding fragment is a murine antibody, 336D8G9 ("A2"), comprising the heavy chain variable region sequence of SEQ ID NO: 23:

```
                                    (SEQ ID NO: 23)
EVQLQQSGAELVRPGASVKLSCPASGFTIKDYYIH

WVKQRPEQGLEWIGRIDPEDGDTEYAPKFQGKATM

TADTSSNTAYLHLSSLTSEDTAVYYCTSNWYSNSY

WGQGTTLTVSS
``` and the light chain variable region sequence of SEQ ID NO: 25:

```
                                    (SEQ ID NO: 25)
DVVMTQTPLSLPVSLGDQASISCRSSQSLVHSNGN

TYLHWYLQKPGQSPKVLIYKVSNRFSGVPDRFSGS

GSGTDFTLKISRVEAEDLGVYFCSQSTHVPYTFGG

GTKLEIK
```

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 23, or its corresponding polynucleotide sequence SEQ ID NO: 24:

```
                                    (SEQ ID NO: 24)
gaggttcagctgcagcagtctggggcagagcttgt gaggccaggggcctcagtcaagttgtcctgcccag cttctggcttcaccattaaagactactatatacac tgggtgaagcagaggcctgagcagggcctggagtg gattggaaggattgatcctgaggatggtgatactg aatatgccccgaagttccagggcaaggccactatg actgcagacacatcctccaacacagcctacctgca cctcagcagcctgacatctgaggacactgccgtct attactgtacttcaaactggtatagtaactcctac tggggccaaggcaccactctcacagtctcctca
``` and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 25, or its corresponding polynucleotide sequence SEQ ID NO: 26:

```
                                    (SEQ ID NO: 26)
gatgttgtgatgacccaaactccactctccctgcc tgtcagtcttggagatcaagcctccatctcttgca gatctagtcagagccttgtacacagtaatggaaac acctatttacattggtacctgcaaaagccaggcca gtctccaaaggtcctgatctacaaagtttccaacc gattttctggggtcccagacaggttcagtggcagt ggatcagggacagatttcacactcaagatcagcag agtggaggctgaggatctgggagtttatttctgct ctcaaagtacacatgttccgtatacgttcggaggg gggaccaagctggaaataaaa
```

In various embodiments of the present invention, the antibody or antigen-binding fragment is a murine antibody, 312A10E5 ("A3"), comprising the heavy chain variable region sequence of SEQ ID NO: 27:

```
                                    (SEQ ID NO: 27)
QIQLVQSGPDLKKPGETVKISCKASGYTFTNYGMS

WVKQAPGKGLKWMGWINTYSGESTYADDFKGRFAF

SLETSASTAYLQINNLKNEDTATYFCARSLNRDTW

FTYWGQGTLVTVSA
``` and the light chain variable region sequence of SEQ ID NO: 29:

```
                                    (SEQ ID NO: 29)
QAVVTQESALSTSPGETVTLTCRSITGAVTTSNYA

NWVQEKPDHLFTGLIGGTNNRAPGVPARFSGSLIG

DKAALTITGAQTEDEAIYFCALWYSNHWVFGGGTK

LTVL
```

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 27, or its corresponding polynucleotide sequence SEQ ID NO: 28:

```
                                    (SEQ ID NO: 28)
cagatccagttggtacagtctggacctgacctgaa gaagcctggagagacagtcaagatctcctgcaagg cttctgggtataccttcacaaactatggaatgagc tgggtgaaacaggctccaggaaagggtttaaagtg gatgggctggataaacacctattctggagagtcaa
```

-continued

```
catatgctgatgacttcaagggacggtttgccttc tctttggaaacctctgccagcactgcctatttgca gatcaacaacctcaaaaatgaggacacggctacat atttctgtgcaagatccctcaaccgggacacctgg tttacttactggggccaagggactctggtcactgt ctctgca
``` and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 29, or its corresponding polynucleotide sequence SEQ ID NO: 30:

```
                                    (SEQ ID NO: 30)
caggctgttgtgactcaggaatctgcactctccac atcacctggtgaaacagtcacactcacttgtcgct caattactggggctgttacaactagtaactatgcc aactgggtccaagaaaaaccagatcatttgttcac tggtctaataggtggtaccaacaaccgagctccag gtgttcctgccagattctcaggctccctgattgga gacaaggctgccctcaccatcacaggggcacagac tgaggatgaggcaatatatttctgtgctctatggt acagcaaccactgggtgttcggtggaggaaccaaa ctgactgtccta
```

In various embodiments, the heavy chain variable domain comprises a sequence of amino acids that is encoded by a polynucleotide that hybridizes under moderately stringent conditions to the complement of a polynucleotide that encodes a heavy chain variable domain having the sequence of SEQ ID NOs: 19, 23 and 27. In another embodiment, the heavy chain variable domain comprises a sequence of amino acids that is encoded by a polynucleotide that hybridizes under stringent conditions to the complement of a polynucleotide that encodes a heavy chain variable domain having the sequence of SEQ ID NOs: 19, 23 and 27. In another embodiment, the light chain variable domain comprises a sequence of amino acids that is encoded by a polynucleotide that hybridizes under moderately stringent conditions to the complement of a polynucleotide that encodes a light chain variable domain having the sequence of SEQ ID NOs: 21, 25 and 29. In another embodiment, the light chain variable domain comprises a sequence of amino acids that is encoded by a polynucleotide that hybridizes under stringent conditions to the complement of a polynucleotide that encodes a light chain variable domain having the sequence of SEQ ID NOs: 21, 25 and 29.

In various embodiments, antibodies of the present invention include antibodies that bind to the same epitope as murine antibody A1. In various embodiments, antibodies of the present invention include antibodies that bind to the same epitope as murine antibody A2. In various embodiments, antibodies of the present invention include antibodies that bind to the same epitope as murine antibody A3.

In various embodiments of the present invention, the antibody or antigen-binding fragment is a murine-human chimeric antibody (derived from murine antibody A3) comprising the heavy chain variable region sequence of SEQ ID NO: 31:

```
                                    (SEQ ID NO: 31)
QVQLVQSGAEVKKPGASVKVSCKASGYTFTNYGMS

WVRQAPGQGLEWMGWINTYSGESTYADDFKGRVTM

TTDTSTSTAYMELRSLRSDDTAVYYCARSLNRDTW

FTYWGQGTLVTVSS
``` and the light chain variable region sequence of SEQ ID NO: 32:

```
                                    (SEQ ID NO: 32)
QTVVTQEPSFSVSPGGTVTLTCRSITGAVTTSNYA

NWYQQTPGQAPRTLIYGTNNRAPGVPDRFSGSILG

NKAALTITGAQADDESDYYCALWYSNHWVFGGGTK

LTVL
```

In various embodiments of the present invention, the antibody or antigen-binding fragment is an isolated humanized antibody or antigen-binding fragment comprising a heavy chain variable region having a sequence identical, substantially identical or substantially similar to SEQ ID NOs: 33-35, and a light chain variable region having the sequence identical, substantially identical or substantially similar to SEQ ID NOs: 36-37. In various embodiments the antibody is a humanized antibody or antigen-binding fragment thereof which comprises the heavy chain variable region having the amino acid sequence set forth in SEQ ID NO: 33 and the light chain variable region having the amino acid sequence set forth in SEQ ID NO: 37. In various embodiments the antibody is a humanized antibody or antigen-binding fragment thereof which comprises the heavy chain variable region having the amino acid sequence set forth in SEQ ID NO: 34 and the light chain variable region having the amino acid sequence set forth in SEQ ID NO: 37. In various embodiments the antibody is a humanized antibody or antigen-binding fragment thereof which comprises the heavy chain variable region having the amino acid sequence set forth in SEQ ID NO: 35 and the light chain variable region having the amino acid sequence set forth in SEQ ID NO: 37.

In various embodiments, the antibodies or antigen-binding fragments thereof comprise a heavy chain variable domain comprising a sequence of amino acids that differs from the sequence of a heavy chain variable domain having the amino acid sequence set forth in SEQ ID NOs: 33-35 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In various embodiments, the antibodies or antigen-binding fragments thereof comprise a heavy chain variable domain comprising a sequence that has at least about 80%, at least about 85%, at least about 90%, 91%, 92%, 93%, 94%, 95%, 96%, 97%, 98%, or at least about 99% identity to the amino acid sequence as set forth in SEQ ID NOs: 33-35.

In various embodiments, an isolated humanized antibody or antigen-binding fragment thereof of the present invention binds to human $ET_4R$ and comprises sequence of amino acids that differs from the sequence of a light chain variable domain having the amino acid sequence set forth in SEQ ID NOs: 36-37 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In various embodiments, the antibodies or antigen-binding fragments thereof comprise a light chain variable domain comprising a sequence that has at least about 80%, at least about 85%, at least about 90%, 91%, 92%, 93%, 94%, 95%, 96%, 97%, 98%, or at least about 99% identity to the amino acid sequence as set forth in SEQ ID NOs: 36-37.

In various embodiments, an isolated humanized antibody or antigen-binding fragment thereof of the present invention binds to human $ET_AR$ and comprises a heavy chain having a sequence identical, substantially identical or substantially similar to SEQ ID NOs: 38, 42 and 44, and a light chain variable region having the sequence identical, substantially identical or substantially similar to SEQ ID NOs: 40 and 46.

In various embodiments of the present invention, the antibody is a humanized IgG comprising the heavy chain sequence ("H1") of SEQ ID NO: 38:

```
                                    (SEQ ID NO: 38)
QVQLVQSGAEVKKPGASVKVSCKASGYTFTNYGMS

WVRQAPGQGLEWMGWINTYSGESTYADDFKGRVTM

TTDTSTSTAYMELRSLRSDDTAVYYCARSLNRDTW

FTYWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK
``` and the light chain sequence ("L3") of SEQ ID NO: 40:

```
                                    (SEQ ID NO: 40)
QTVVTQEPSFSVSPGGTVTLTCRSITGAVTTSNYA

NWVQETPGQAPRGLIGGTNNRAPGVPDRFSGSILG

NKAALTITGAQADDEADYFCALWYSNHWVFGGGTK

LTVLGQPKAAPSVTLFPPSSEELQANKATLVCLIS

DFYPGAVTVAWKADSSPVKAGVETTTPSKQSNNKY

AASSYLSLTPEQWKSHRSYSCQVTHEGSTVEKTVA

PTECS
```

In certain alternative embodiments, the antibody is an antibody comprising a heavy chain and a light chain, wherein the heavy chain comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 38, or its corresponding polynucleotide sequence SEQ ID NO: 39:

```
                                    (SEQ ID NO: 39)
caggtgcagctggtgcagtctggagcagaggtgaa gaagccaggagcctctgtgaaggtgagctgcaagg cctccggctacaccttcacaaactatggcatgagc tgggtgcggcaggcacctggacagggactggagtg gatgggctggatcaatacatactccggcgagtcta cctatgccgacgacttcaagggcagggtgacaatg accacagacacctctacaagcaccgcctacatgga gctgcggagcctgagatccgacgataccgccgtgt actattgtgccaggtccctgaaccgcgatacatgg ttcacctattggggccagggcacactggtgaccgt gagctccgccagcaccaagggcccttccgtgtttc cactggccccctcctctaaatccacatctggcggc accgccgccctgggctgtctggtgaaggactactt cccagagcctgtgacagtgtcctggaactctggcg ccctgacatccggcgtgcacacatttccagccgtg ctgcagagctccggcctgtacagcctgtctagcgt ggtgacagtgccctcctctagcctgggcacacaga cctatatctgcaacgtgaatcacaagccaagcaat accaaggtggacaagaaggtggagcccaagtcctg tgataagacacacacctgcccccccttgtcctgctc ccgagctgctgggcggccctagcgtgttcctgttt ccacccaagcctaaggacaccctgatgatctcccg gacacccgaggtgacctgcgtggtggtggacgtgt ctcacgaggatcctgaggtgaagttcaactggtat gtggatggcgtggaggtgcacaatgccaagaccaa gcccagagaggagcagtacaactctacatataggg tggtgagcgtgctgaccgtgctgcaccaggactgg ctgaacggcaaggagtataagtgcaaggtgtccaa taaggccctgcccgcccccatcgagaagacaatca gcaaggccaagggccagcctcgggagccacaggtg tacaccctgcctccatccagagacgagctgacaaa gaaccaggtgtctctgacatgtctggtgaagggct tctatcctagcgatatcgccgtggagtgggagtcc aatggccagccagagaacaattacaagaccacacc ccctgtgctggactccgatggctccttcttttctgt attccaagctgaccgtggataagtctcggtggcag cagggcaacgtgttcagctgttc cgtgatgcacg aagccctgcataatcactatactcagaaatccctg tccctgtcacctggaaag
``` and wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 40, or its corresponding polynucleotide sequence SEQ ID NO: 41:

```
                              (SEQ ID NO: 41)
cagacagtggtgacccaggagcctagcttctccgt gtctccaggaggaaccgtgacactgacctgcaggt ctatcacaggcgccgtgaccacaagcaactacgcc aattgggtgcaggagacaccaggacaggcaccaag gggactgatcggaggaaccaacaataagggcaccag gagtgcctgaccggttcagcggatccatcctggga aacaaggccgccctgacaatcaccggagcacaggc agacgatgaggcagattacttctgtgccctgtggt attccaatcactgggtgtttggcggcggcacaaag ctgaccgtgctggggcagcccaaggccgctcctag cgtgacactgtttcccccttcctccgaggagctgc aggccaacaaggccaccctggtgtgcctgatctcc gacttctatcctggcgccgtgacagtggcctggaa ggctgattctagcccagtgaaggctggcgtggaga ccacaacccctccaagcagtctaacaataagtat gccgcttcctcttacctgagcctgacaccagagca gtggaagtcccaccggtcttacagctgccaggtca ctcacgaaggctctaccgtggaaaagacagtcgca cccaccgaatgctcatgataagcttaagggttcga tccct
```

In various embodiments of the present invention, the antibody is a humanized IgG comprising the heavy chain sequence ("H2") of SEQ ID NO: 42:

```
                              (SEQ ID NO: 42)
QVQLVQSGAEVKKPGASVKVSCKASGYTFTNYGMS

WVRQAPGQGLEWMGWINTYSGESTYADDFKGRFTM

TLDTSTSTAYMELRSLRSDDTAVYFCARSLNRDTW

FTYWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK
``` and the light chain sequence ("L3") of SEQ ID NO: 40.

In certain alternative embodiments, the antibody is an antibody comprising a heavy chain and a light chain, wherein the heavy chain comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 42, or its corresponding polynucleotide sequence SEQ ID NO: 43:

```
                              (SEQ ID NO: 43)
caggtgcagctggtgcagtctggagcagaggtgaa gaagccaggagcctctgtgaaggtgagctgcaagg cctccggctacaccttcacaaactatggcatgagc tgggtgcggcaggcacctggacagggactggagtg gatgggctggatcaatacatactccggcgagtcta cctatgccgacgatttcaagggcaggtttaccatg acactggacacctctacaagcaccgcctacatgga gctgcggagcctgagatccgacgatacagccgtgt atttctgtgccaggtccctgaaccgcgatacatgg tttacctactggggccagggcacactggtgaccgt gagctccgccagcaccaagggcccttccgtgtttc cactggcccctcctctaaatccacatctggcggc accgccgccctgggctgtctggtgaaggactactt cccagagcctgtgacagtgtcctggaactctggcg ccctgacatccggcgtgcacacatttccagccgtg ctgcagagctccggcctgtacagcctgtctagcgt ggtgacagtgccctcctctagcctgggcacacaga cctatatctgcaacgtgaatcacaagccaagcaat accaaggtggacaagaaggtggagcccaagtcctg tgataagacacacacctgcccccccttgtcctgctc ccgagctgctgggcggccctagcgtgttcctgttt ccacccaagcctaaggacaccctgatgatctcccg gacacccgaggtgacctgcgtggtggtggacgtgt ctcacgaggatcctgaggtgaagttcaactggtat gtggatggcgtggaggtgcacaatgccaagaccaa gcccagagaggagcagtacaactctacatataggg tggtgagcgtgctgaccgtgctgcaccaggactgg ctgaacggcaaggagtataagtgcaaggtgtccaa taaggccctgcccgcccccatcgagaagacaatca gcaaggccaagggccagcctcgggagccacaggtg tacaccctgcctccatccagagacgagctgacaaa gaaccaggtgtctctgacatgtctggtgaagggct tctatcctagcgatatcgccgtggagtgggagtcc aatggccagccagagaacaattacaagaccacacc ccctgtgctggactccgatggctccttcttttctgt attccaagctgaccgtggataagtctcggtggcag
```

```
cagggcaacgtgttcagctgttccgtgatgcacga agccctgcataatcactatactcagaaatccctgt ccctgtcacctggaaag
``` and wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 40, or its corresponding polynucleotide sequence SEQ ID NO: 41.

In various embodiments of the present invention, the antibody is a humanized IgG comprising the heavy chain sequence ("H3") of SEQ ID NO: 44:

```
                              (SEQ ID NO: 44)
QVQLVQSGAEVKKPGASVKVSCKASGYTFTNYGMS

WVRQAPGQGLEWMGWINTYSGESTYADDFKGRFTF

TLDTSTSTAYMELRSLRSDDTATYFCARSLNRDTW

FTYWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK
``` and the light chain sequence ("L3") of SEQ ID NO: 40.

In certain alternative embodiments, the antibody is an antibody comprising a heavy chain and a light chain, wherein the heavy chain comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 44, or its corresponding polynucleotide sequence SEQ ID NO: 45:

```
                              (SEQ ID NO: 45)
caggtgcagctggtgcagtctggagcagaggtgaa gaagccaggagcctctgtgaaggtgagctgcaagg cctccggctacaccttcacaaactatggcatgagc tgggtgcggcaggcacctggacagggactggagtg gatgggctggatcaatacatactccggcgagtcta cctatgccgacgacttcaagggcaggttcaccttt acactggacacctctacaagcaccgcctacatgga gctgcggagcctgagatccgacgatacagccacct atttctgtgccaggtccctgaaccgcgatacatgg tttacctactggggccagggcacactggtgaccgt
```

```
gagctccgccagcaccaagggcccttccgtgtttc cactggccccctcctctaaatccacatctggcggc accgccgccctgggctgtctggtgaaggactactt cccagagcctgtgacagtgtcctggaactctggcg ccctgacatccggcgtgcacacatttccagccgtg ctgcagagctccggcctgtacagcctgtctagcgt ggtgacagtgccctcctctagcctgggcacacaga cctatatctgcaacgtgaatcacaagccaagcaat accaaggtggacaagaaggtggagcccaagtcctg tgataagacacacacctgccccccttgtcctgctc ccgagctgctgggcggccctagcgtgttcctgttt ccacccaagcctaaggacaccctgatgatctcccg gacacccgaggtgacctgcgtggtggtggacgtgt ctcacgaggatcctgaggtgaagttcaactggtat gtggatggcgtggaggtgcacaatgccaagaccaa gcccagagaggagcagtacaactctacatataggg tggtgagcgtgctgaccgtgctgcaccaggactgg ctgaacggcaaggagtataagtgcaaggtgtccaa taaggccctgcccgcccccatcgagaagacaatca gcaaggccaagggccagcctcgggagccacaggtg tacaccctgcctccatccagagacgagctgacaaa gaaccaggtgtctctgacatgtctggtgaagggct tctatcctagcgatatcgccgtggagtgggagtcc aatggccagccagagaacaattacaagaccacacc ccctgtgctggactccgatggctccttctttctgt attccaagctgaccgtggataagtctcggtggcag caggcaacgtgttcagctgttccgtgatgcacga agccctgcataatcactatactcagaaatccctgt ccctgtcacctggaaag
``` and wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 40, or its corresponding polynucleotide sequence SEQ ID NO: 41.

In various embodiments of the present disclosure, the antibody may be an anti-ET$_4$R antibody that has the same or higher antigen-binding affinity as that of the antibody comprising the heavy chain sequence as set forth in any of SEQ ID NOs: 38, 42 and 44. In various embodiments, the antibody may be an anti-ET$_4$R antibody which binds to the same epitope as the antibody comprising the heavy chain sequence as set forth in any of SEQ ID NOs: 38, 42 and 44. In various embodiments, the antibody is an anti-ET$_4$R antibody which competes with the antibody comprising the heavy chain sequence as set forth in any of SEQ ID NOs: 38, 42 and 44. In various embodiments, the antibody may be an anti-ET$_A$R antibody which comprises at least one (such as two or three) CDRs of the heavy chain sequence as set forth in any of SEQ ID NOs: 38, 42 and 44.

In various embodiments, the antibody contains an heavy chain amino acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 38, 42 and 44. In various embodiments, the antibody contains a nucleic acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 39, 43 and 45.

In various embodiments of the present disclosure the antibody may be an anti-ET$_A$R antibody that has the same or higher antigen-binding affinity as that of the antibody comprising the light chain sequence as set forth in any of SEQ ID NOs: 40 and 46. In various embodiments, the antibody may be an anti-ET$_A$R antibody which binds to the same epitope as the antibody comprising the light chain sequence as set forth in any of SEQ ID NOs: 40 and 46. In various embodiments, the antibody is an anti-ET$_A$R antibody which competes with the antibody comprising the light chain sequence as set forth in any of SEQ ID NOs: 40 and 46. In various embodiments, the antibody may be an anti-ET$_A$R antibody which comprises at least one (such as two or three) CDRs of the light chain sequence as set forth in any of SEQ ID NOs: 40 and 46.

In various embodiments, the antibody contains an light chain amino acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 40 and 46. In various embodiments, the antibody contains a nucleic acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 41 and 47.

In various embodiments, an isolated humanized antibody or antigen-binding fragment thereof of the present invention binds to human ET$_A$R and comprises a heavy chain variable region having a sequence identical, substantially identical or substantially similar to SEQ ID NOs: 38, 42 and 44, and a light chain variable region having the sequence identical, substantially identical or substantially similar to SEQ ID NO: 40. In various embodiments, an isolated humanized antibody or antigen-binding fragment thereof of the present invention binds to human ET$_A$R and comprises the heavy chain sequence set forth in SEQ ID NO: 38, and the light chain sequence set forth in SEQ ID NO: 40. In various embodiments, an isolated humanized antibody or antigen-binding fragment thereof of the present invention binds to human ET$_A$R and comprises the heavy chain sequence set forth in SEQ ID NO: 42, and the light chain sequence set forth in SEQ ID NO: 40. In various embodiments, an isolated humanized antibody or antigen-binding fragment thereof of the present invention binds to human ET$_A$R and comprises the heavy chain sequence set forth in SEQ ID NO: 44, and the light chain sequence set forth in SEQ ID NO: 40.

Antibodies or antigen-binding fragments thereof of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a IgA-, IgD-, IgE-, IgG- and IgM-type heavy chain constant region. In various embodiments, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16, 2002.

In various embodiments, an antibody of the invention further comprises a light chain kappa or lambda constant domain, or a fragment thereof, and further comprises a heavy chain constant domain, or a fragment thereof. Sequences of the light chain constant region and heavy chain constant region used in the exemplified antibodies, and polynucleotides encoding them, are provided below.

```
Light Chain (Kappa) Constant Region
                            (SEQ ID NO: 48)
RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC

Light Chain (Lambda) Constant Region
                            (SEQ ID NO: 49)
GQPKAAPSVTLFPPSSEELQANKATLVCLISDFYP

GAVTVAWKADSSPVKAGVETTTPSKQSNNKYAASS

YLSLTPEQWKSHRSYSCQVTHEGSTVEKTVAPTEC

S

Heavy Chain Constant Region
                            (SEQ ID NO: 50)
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
```

Antibodies of the present invention may also be described or specified in terms of their cross-reactivity. Antibodies that bind ET$_A$Rs, which have at least 95%, at least 90%, at least 85%, at least 80%, at least 75%, at least 70%, at least 65%, at least 60%, at least 55%, and at least 50% identity (as calculated using methods known in the art and described herein) to human ET$_A$R are also included in the present invention.

Further included in the present invention are antibodies that bind to the same epitope as the anti-$ET_AR$ antibodies of the present invention. To determine if an antibody can compete for binding to the same epitope as the epitope bound by the anti-$ET_AR$ antibodies of the present invention, a cross-blocking assay, e.g., a competitive ELISA assay, can be performed. In an exemplary competitive ELISA assay, $ET_AR$ coated on the wells of a microtiter plate is pre-incubated with or without candidate competing antibody and then the biotin labeled anti-$ET_AR$ antibody of the invention is added. The amount of labeled anti-$ET_AR$ antibody bound to the $ET_AR$ antigen in the wells is measured using avidin-peroxidase conjugate and appropriate substrate. The antibody can be labeled with a radioactive or fluorescent label or some other detectable and measurable label. The amount of labeled anti-$ET_AR$ antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an anti-$ET_AR$ antibody of the invention if the candidate antibody can block binding of the $ET_AR$ antibody by at least 20%, by at least 30%, by at least 40%, or by at least 50% as compared to the control performed in parallel in the absence of the candidate competing antibody. It will be understood that variations of this assay can be performed to arrive at the same quantitative value.

In certain alternative embodiments, the antibodies of the present invention can be engineered by modifying one or more residues within one or both variable regions (i.e., $V_H$ and/or $V_L$), or by modifying residues within the constant region(s), e.g., to alter the effector function(s) of the antibody. In various embodiments, the variable region of the antibody will by modified by performing CDR grafting using framework sequences can be obtained from public DNA databases or published references that include germline antibody gene sequences (e.g., Tomlinson, I. M., et al., J. Mol. Biol. 227:776-798, 1992; and Cox, J. P. L. et al., Eur. J. Immunol. 24:827-836, 1994; the contents of each of which are expressly incorporated herein by reference). In various embodiments, the antibodies may be modified using site-directed mutagenesis or PCR-mediated mutagenesis to introduce a mutation(s) in the VH and/or VL which improves binding affinity and/or decreases immunogenicity. In various embodiments, the antibodies may be modified in the Fc region for purposes of altering the serum half-life, complement fixation, Fc receptor binding, and/or antigen-dependent cellular cytotoxicity of the antibody. In various embodiments, the antibodies may be modified for purposes of modifying the glycosylation of the antibody. Methods for performing each of the modifications described herein, and others, are well known to the skilled artisan.

Pharmaceutical Compositions

In another aspect, the present invention provides a pharmaceutical composition comprising an antibody or antigen-binding fragment thereof as described above. The pharmaceutical compositions, methods and uses of the invention thus also encompass embodiments of combinations (co-administration) with other active agents, as detailed below.

Generally, the antibodies, or antigen-binding fragments thereof antibodies of the present invention are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Various embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-ETR antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurized container, pump, spray, atomizer (preferably an atomizer using electrohydrodynamics to produce a fine mist), or nebulizer, with or without the use of a suitable propellant, or as nasal drops.

The pressurized container, pump, spray, atomizer, or nebulizer generally contains a solution or suspension of an antibody of the invention comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the compound of the invention, a suitable powder base and a performance modifier.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate- and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Pharmaceutical compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, the antibody or antigen-binding fragment thereof is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract. Compositions comprising antibodies or antigen-binding fragments thereof may be prepared as described generally in Remington's Pharmaceutical Sciences, 18th Ed. 1990 (Mack Publishing Co. Easton Pa. 18042) at Chapter 89, which is herein incorporated by reference.

In various embodiments, the pharmaceutical compositions are formulated as orally deliverable tablets containing antibodies or antigen-binding fragments thereof in admixture with non-toxic pharmaceutically acceptable excipients which are suitable for manufacture of tablets. These excipients may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

In various embodiments, the pharmaceutical compositions are formulated as hard gelatin capsules wherein the antibody or antigen-binding fragment thereof is mixed with an inert solid diluent, for example, calcium carbonate, calcium phosphate, or kaolin or as soft gelatin capsules wherein the antibody or antigen-binding fragment thereof is mixed with an aqueous or an oil medium, for example, *arachis* oil, peanut oil, liquid paraffin or olive oil.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic Uses

In another aspect, the present invention relates to methods of treating a subject suffering from a $ET_4R$-associated disorder, comprising administering to said subject a therapeutically effective amount (either as monotherapy or in a combination therapy regimen) of an antibody or antigen-binding fragment thereof of the present invention. In various embodiments, the subject is a human subject.

In various embodiments, the $ET_4R$-associated disorder is a metabolic disorder selected from the group consisting of diabetes, diabetic myopathy, diabetic nephropathy, diabetic neuropathy, diabetic retinopathy, obesity, dyslipidemia, sarcopenic obesity, fatty liver disease (e.g., nonalcoholic fatty liver disease (NAFLD); nonalcoholic steatohepatitis (NASH)), insulin resistance, and hemochromatosis.

In various embodiments, the $ET_4R$-associated disorder is a cardiovascular disease selected from the group consisting of angina, heart attack (myocardial infarction), atherosclerosis, heart failure, cardiovascular disease, rheumatic heart disease, cardiac arrhythmias (abnormal heart rhythms), cerebrovascular disease, congenital heart defects, cardiomyopathy, left ventricular hypertrophy, right ventricular hypertrophy, post-infarction heart rupture, infections of the heart, coronary artery disease, peripheral arterial disease, renal artery stenosis, aortic aneurysm, myocardial diseases, heart valve disorders, myocarditis, pericarditis, and pulmonary arterial hypertension (PAH).

"Therapeutically effective amount" or "therapeutically effective dose" refers to that amount of the therapeutic agent being administered which will relieve to some extent one or more of the symptoms of the disorder being treated.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of the antibodies or antigen-binding fragments thereof of the disclosure can be in the range of 0.5-1200 mg per subject, 0.5-1100 mg per subject, 0.5-1000 mg per subject, 0.5-900 mg per subject, 0.5-800 mg per subject, 0.5-700 mg per subject, 0.5-600 mg per subject, 0.5-500 mg per subject, 0.5-400 mg per subject, 0.5-300 mg per subject, 0.5-200 mg per subject, 0.5-100 mg per subject, 0.5-50 mg per subject, 1-1200 mg per subject, 1-1100 mg per subject, 1-1000 mg per subject, 1-900 mg per subject, 1-800 mg per subject, 1-700 mg per subject, 1-600 mg per subject, 1-500 mg per subject, 1-400 mg per subject, 1-300 mg per subject, 1-200 mg per subject, 1-100 mg per subject, or 1-50 mg per subject depending, of course, on the mode of administration. For example, an intravenous monthly dose can require about 1-1000 mg/subject. In various embodiments, the antibodies or antigen-binding fragments thereof of the disclosure can be administered at about 1-200 mg per subject, 1-150 mg per subject or 1-100 mg/subject. The total monthly dose can be administered in single or divided doses and can, at the physician's discretion, fall outside of the typical ranges given herein.

In various embodiments, a non-limiting daily dosing range for a therapeutically or prophylactically effective amount of an antibody or antigen-binding fragment thereof of the disclosure can be 0.001 to 100 mg/kg, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight.

For repeated administrations over several days or longer, depending on the condition, the treatment is sustained until a desired suppression of symptoms occurs or until sufficient therapeutic levels are achieved, for example, to reduce pain. An exemplary dosing regimen comprises administering an initial dose of about 2 mg/kg, followed by a weekly maintenance dose of about 1 mg/kg of the anti-$ET_AR$ antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one-four times a week is contemplated. The progress of this therapy is easily monitored by conventional techniques and assays. The dosing regimen (including the $ET_AR$ antagonist(s) used) can vary over time. In various embodiments, the appropriate dosage of an anti-$ET_AR$ antagonist antibody will depend on the anti-$ET_AR$ antagonist antibody (or compositions thereof) employed, the type and severity of headache (e.g., migraine) to be treated, whether the agent is administered for preventive or therapeutic purposes, previous therapy, the patient's clinical history and response to the agent, and the discretion of the attending physician. Typically, the clinician will administer an anti-$ET_AR$ antagonist antibody, until a dosage is reached that achieves the desired result. Dose and/or frequency can vary over course of treatment.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In various embodiments, the total dose administered will achieve a plasma antibody concentration in the range of, e.g., about 1 to 1000 µg/ml, about 1 to 750 µg/ml, about 1 to 500 µg/ml, about 1 to 250 µg/ml, about 10 to 1000 µg/ml, about 10 to 750 µg/ml, about 10 to 500 µg/ml, about 10 to 250 µg/ml, about 20 to 1000 µg/ml, about 20 to 750 µg/ml, about 20 to 500 µg/ml, about 20 to 250 µg/ml, about 30 to 1000 µg/ml, about 30 to 750 µg/ml, about 30 to 500 µg/ml, about 30 to 250 µg/ml.

Toxicity and therapeutic index of the pharmaceutical compositions of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

In various embodiments, single or multiple administrations of the pharmaceutical compositions are administered depending on the dosage and frequency as required and tolerated by the subject. In any event, the composition should provide a sufficient quantity of at least one of the antibodies or antigen-binding fragments thereof disclosed herein to effectively treat the subject. The dosage can be administered once but may be applied periodically until either a therapeutic result is achieved or until side effects warrant discontinuation of therapy.

The dosing frequency of the administration of the antibody or antigen-binding fragment thereof pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the antibodies or antigen-binding fragments thereof of the disclosure and one or more other therapeutic agents, is intended to mean, and does refer to and include the following: simultaneous administration of such combination of antibodies or antigen-binding fragments thereof of the disclosure and therapeutic agent(s) to a subject in need of treatment, when such components are formulated together into a single dosage form which releases said components at substantially the same time to said subject; substantially simultaneous administration of such combination of antibodies or antigen-binding fragments thereof of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of antibodies or antigen-binding fragments thereof of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of antibodies or antigen-binding fragments thereof of the disclosure and therapeutic agent(s) to a subject in need of treatment, when such components are formulated together into into a single dosage form which releases said components in a controlled manner whereupon they are concurrently, consecutively, and/or overlappingly released at the same and/or different times to said subject, where each part may be administered by either the same or a different route.

In another aspect, the present invention relates to combination therapies designed to treat a metabolic disorder in a subject, comprising administering to the subject a therapeutically effective amount of an isolated antibody or antigen-binding fragment of the present invention, and (b) administering a glucose-lowering agent. In various embodiments, the glucose-lowering agent is selected from anti-diabetic agents, anti-hyperglycemic agents, lipid lowering agents, anti-hypertensive agents, and anti-obesity agents. In various embodiments, the glucose-lowering agent is selected from biguanides, sulfonylureas, meglitinides, thiazolidinediones (TZDs), α-glucosidase inhibitors, DPP-4 inhibitors, bile acid sequestrants, dopamine-2 agonists, SGLT2 inhibitors, GLP-1R agonists, amylin mimetics, and insulins.

In another aspect, the present invention provides combination therapies designed to treat a cardiovascular disease in a subject, comprising (a) administering to said subject a therapeutically effective amount of an isolated antibody or antigen-binding fragment of the present invention, and (b) administering a second agent selected from the group consisting of antihypertensive agents, agents for treating chronic heart failure, atherosclerosis or related diseases. In various embodiments such agents contemplated for use include, but are not limited to, bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetamide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretamide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), antiplatelets agents (such as aspirin, clopidogrel, ticlopidine, dipyridamole, cilostazol, ethyl icosapentate, sarpogrelate, dilazep, trapidil, beraprost and the like), and neuregulins (NRG-1, NRG-2, NRG-3 and NRG-4) and isoforms thereof.

In various embodiments, the combination therapy comprises administering the antibody or antigen-binding fragment thereof and the one or more additional therapies simultaneously. In various embodiments, antibody or antigen-binding fragment thereof composition and the one or more additional therapies are administered sequentially, i.e., the antibody or antigen-binding fragment thereof composition is administered either prior to or after the administration of the one or more additional therapies.

In various embodiments, the administrations of the antibody or antigen-binding fragment thereof composition and the one or more additional therapies are concurrent, i.e., the administration period of the antibody or antigen-binding fragment thereof composition and the one or more additional therapies overlap with each other.

In various embodiments, the administrations of the antibody or antigen-binding fragment thereof composition and the one or more additional therapies are non-concurrent. For example, in various embodiments, the administration of the antibody or antigen-binding fragment thereof composition is terminated before the one or more additional therapies is administered. In various embodiments, the administration of the one or more additional therapies is terminated before the antibody or antigen-binding fragment thereof composition is administered.

When the antibody or antigen-binding fragment thereof disclosed herein is administered in combination with one or more additional therapies, either concomitantly or sequentially, such antibody or antigen-binding fragment thereof may enhance the therapeutic effect of the one or more additional therapies or overcome cellular resistance to the one or more additional therapies. This allows for decreased dosage or duration of the one or more additional therapies, thereby reducing the undesirable side effects, or restores the effectiveness of the one or more additional therapies.

Diagnostic Uses

In another aspect, the present invention provides a method for detecting in vitro or in vivo the presence of human ETR peptide in a sample, e.g., for diagnosing a human ETR-related disorder. In some methods, this is achieved by contacting a sample to be tested, along with a control sample, with a human sequence antibody or a human monoclonal antibody of the invention, or an antigen-binding portion thereof (or a bispecific or multispecific molecule), under conditions that allow for formation of a complex between the antibody and human ETR. Complex formation is then detected (e.g., using an ELISA) in both samples, and any statistically significant difference in the formation of complexes between the samples is indicative the presence of human ETR antigen in the test sample.

In various embodiments, methods are provided for detecting a ETR-related disorder or confirming the diagnosis of a ETR-related disorder in a subject. The method includes contacting a biological sample from the subject with an isolated antibody or antigen-biding fragment thereof of the invention and detecting binding of the isolated human monoclonal antibody or antigen-binding fragment thereof to the sample. An increase in binding of the isolated human monoclonal antibody or antigen-binding fragment thereof to the sample as compared to binding of the isolated human monoclonal antibody or antigen-binding fragment thereof to a control sample detects a ETR-related disorder in the subject or confirms the diagnosis of a ETR-related disorder in the subject. The control can be a sample from a subject known not to have a ETR-related disorder, or a standard value. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, and spinal fluid.

In one embodiment, a kit is provided for detecting ETR in a biological sample, such as a blood sample. Kits for detecting a polypeptide will typically comprise a human antibody that specifically binds ETR, such as any of the antibodies disclosed herein. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds ETR. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting ETR in a biological sample generally includes the steps of contacting the biological sample with an antibody which specifically reacts, under immunologically reactive conditions, to ETR. The antibody is allowed to specifically bind under immunologically reactive conditions to form an immune complex, and the presence of the immune complex (bound antibody) is detected directly or indirectly.

In various embodiments, the antibodies or antigen-binding fragments can be labeled or unlabeled for diagnostic purposes. Typically, diagnostic assays entail detecting the formation of a complex resulting from the binding of an antibody to ETR. The antibodies can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos.

3,817,827; 3,850,752; 3,901,654; and 4,098,876). When unlabeled, the antibodies can be used in assays, such as agglutination assays. Unlabeled antibodies can also be used in combination with another (one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

The antibody or antigen-binding fragment provided herein may also be used in a method of detecting the susceptibility of a mammal to certain diseases. To illustrate, the method can be used to detect the susceptibility of a mammal to diseases which progress based on the amount of ETR present on cells and/or the number of ETR-positive cells in a mammal. In one embodiment, the application provides a method of detecting susceptibility of a mammal to a tumor. In this embodiment, a sample to be tested is contacted with an antibody which binds to ETR or portion thereof under conditions appropriate for binding of said antibody thereto, wherein the sample comprises cells which express ETR in normal individuals. The binding of antibody and/or amount of binding is detected, which indicates the susceptibility of the individual to a tumor, wherein higher levels of receptor correlate with increased susceptibility of the individual to a tumor.

In various embodiments, the antibodies or antigen-binding fragments are attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

Immunoscintigraphy using antibodies or antigen-binding fragments directed at ETR may be used to detect and/or diagnose cancers and vasculature. For example, monoclonal antibodies against the ETR marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically, 0.1-100 millicuries per dose of imaging agent, or 1-10 millicuries, or 2-5 millicuries are administered. Thus, the compositions disclosed are useful as imaging agents comprising a targeting moiety conjugated to a radioactive moiety comprise 0.1-100 millicuries, in some embodiments 1-10 millicuries, in some embodiments 2-5 millicuries, in some embodiments 1-5 millicuries.

Immunoconjugates

The application further provides immunoconjugates comprising an antibody or antigen-binding fragment thereof of the present invention conjugated (or linked) directly or indirectly to an effector molecule. In this regard, the term "conjugated" or "linked" refers to making two polypeptides into one contiguous polypeptide molecule. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. In various embodiments, an antibody or antigen-binding fragment is joined to an effector molecule. In other embodiments, an antibody or antigen-binding fragment joined to an effector molecule is further joined to a lipid, a protein or peptide to increase its half-life in the body. Accordingly in various embodiments, the antibodies of the present disclosure may be used to deliver a variety of effector molecules.

The effector molecule can be a detectable label, an immunotoxin, cytokine, chemokine, therapeutic agent, or chemotherapeutic agent.

Specific, non-limiting examples of immunotoxins include, but are not limited to, abrin, ricin, *Pseudomonas* exotoxin (PE, such as PE35, PE37, PE38, and PE40), diphtheria toxin (DT), botulinum toxin, cholix toxin, or modified toxins thereof, or other toxic agents that directly or indirectly inhibit cell growth or kill cells.

A "cytokine" is class of proteins or peptides released by one cell population which act on another cell as intercellular mediators. Cytokines can act as an immune-modulating agent. Examples of cytokines include lymphokines, monokines, growth factors and traditional polypeptide hormones. Thus, embodiments may utilize an interferon (e.g., IFN-$\alpha$, IFN-$\beta$, and IFN-$\gamma$); tumor necrosis factor super family (TNFSF) member; human growth hormone; thyroxine; insulin; proinsulin; relaxin; prorelaxin; follicle stimulating hormone (FSH); thyroid stimulating hormone (TSH); luteinizing hormone (LH); hepatic growth factor; prostaglandin, fibroblast growth factor; prolactin; placental lactogen, OB protein; TNF-$\alpha$; TNF-$\beta$; integrin; thrombopoietin (TPO); a nerve growth factor such as NGF-$\beta$; platelet-growth factor; TGF-$\alpha$; TGF-$\beta$; insulin-like growth factor-I and -II; erythropoietin (EPO); colony stimulating factors (CSFs) such as macrophage-CSF (M-CSF); granulocyte-macrophage-CSF (GM-CSF); and granulocyte-CSF (G-CSF); an interleukin (IL-1 to IL-21), kit-ligand or FLT-3, angiostatin, thrombospondin, or endostatin. These cytokine include proteins from natural sources or from recombinant cell culture and biologically active equivalents of the native sequence cytokines.

Chemokines can also be conjugated to the antibodies disclosed herein. Chemokines are a superfamily of small (approximately about 4 to about 14 kDa), inducible and secreted pro-inflammatory cytokines that act primarily as chemoattractants and activators of specific leukocyte cell subtypes. Chemokine production is induced by inflammatory cytokines, growth factors and pathogenic stimuli. The chemokine proteins are divided into subfamilies (alpha, beta, and delta) based on conserved amino acid sequence motifs and are classified into four highly conserved groups—CXC, CC, C and CX3C, based on the position of the first two cysteines that are adjacent to the amino terminus. To date, more than 50 chemokines have been discovered and there are at least 18 human seven-transmembrane-domain (7TM) chemokine receptors. Chemokines of use include, but are not limited to, RANTES, MCAF, MCP-1, and fractalkine.

The therapeutic agent can be a chemotherapeutic agent. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Useful chemotherapeutic agents for the preparation of immunoconjugates include auristatin, dolastatin, MMAE, MMAF, AFP, DM1, AEB, doxorubicin, daunorubicin, methotrexate, melphalan, chlorambucil, vinca alkaloids, 5-fluorouridine, mitomycin-C, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbazine, topotecan, nitrogen mustards, cytoxan, etoposide, BCNU, irinotecan, camptothecins, bleomycin, idarubicin, dactinomycin, plicamycin, mitoxantrone, asparaginase, vinblastine, vincristine, vinorelbine, paclitaxel, and docetaxel and salts, solvents and derivatives thereof. In various embodiments, the chemotherapeutic agent is auristatin E (also known in the art as dolastatin-10) or a derivative thereof as well as pharmaceutically salts or solvates thereof. Typical auristatin derivatives include DM1, AEB, AEVB, AFP, MMAF, and MMAE. The synthesis and structure of auristatin E and its derivatives, as well as linkers, are described in, e.g., U.S. Patent Application Publication No. 20030083263; U.S. Patent Application Publication No. 20050238629; and U.S. Pat. No. 6,884,869 (each of which is incorporated by reference herein in its entirety). In various embodiments, the therapeutic agent is an auristatin or an auristatin derivative. In various embodiments, the auristatin derivative is dovaline-valine-dolaisoleunine-dolaproine-phenylalanine (MMAF) or monomethyauristatin E (MMAE). In various embodiments, the therapeutic agent is a maytansinoid or a maytansinol analogue. In various embodiments, the maytansinoid is DM1.

The effector molecules can be linked to an antibody or antigen-binding fragment of the present invention using any number of means known to those of skill in the art. Both covalent and noncovalent attachment means may be used. The procedure for attaching an effector molecule to an antibody varies according to the chemical structure of the effector molecule. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

Procedures for conjugating the antibodies with the effector molecules have been previously described and are within the purview of one skilled in the art. For example, procedures for preparing enzymatically active polypeptides of the immunotoxins are described in WO84/03508 and WO85/03508, which are hereby incorporated by reference for purposes of their specific teachings thereof. Other techniques are described in Shih et al., Int. J. Cancer 41:832-839 (1988); Shih et al., Int. J. Cancer 46:1101-1106 (1990); Shih et al., U.S. Pat. No. 5,057,313; Shih Cancer Res. 51:4192, International Publication WO 02/088172; U.S. Pat. No. 6,884,869; International Patent Publication WO 2005/081711; U.S. Published Application 2003-0130189 A; and US Patent Application No. 20080305044, each of which is incorporated by reference herein for the purpose of teaching such techniques.

An immunoconjugate of the present invention retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate is also referred to as an antibody drug conjugate (ADC).

Bispecific Molecules

In another aspect, the present invention features bispecific molecules comprising an anti-ETR antibody, or antigen-binding fragment thereof, of the invention. An antibody of the invention, or antigen-binding fragment thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results. In various embodiments, the invention includes bispecific molecules capable of binding both to FcγR or FcαR expressing effector cells (e.g., monocytes, macrophages or polymorphonuclear cells (PMNs)), and to target cells expressing PD. In such embodiments, the bispecific molecules target ETR expressing cells to effector cell and trigger Fc receptor-mediated effector cell activities, e.g., phagocytosis of an ETR expressing cells, antibody dependent cell-mediated cytotoxicity (ADCC), cytokine release, or generation of superoxide anion. Methods of preparing the bispecific molecules of the present invention are well known in the art.

Polynucleotides and Antibody Expression

The application further provides polynucleotides comprising a nucleotide sequence encoding an anti-ETR antibody or antigen-binding fragment thereof. Because of the degeneracy of the genetic code, a variety of nucleic acid sequences encode each antibody amino acid sequence. The application further provides polynucleotides that hybridize under stringent or lower stringency hybridization conditions, e.g., as defined herein, to polynucleotides that encode an antibody that binds to human ETR.

Stringent hybridization conditions include, but are not limited to, hybridization to filter-bound DNA in 6×SSC at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR. In one embodiment, the codons that are used comprise those that are typical for human or mouse (see, e.g., Nakamura, Y., Nucleic Acids Res. 28: 292 (2000)).

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

The present invention is also directed to host cells that express a ETR and/or the anti-ETR antibodies of the invention. A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably-linked in one vector or, alternatively, the heavy chain and the light chain may be expressed independently from different promoters to which they are operably-linked in two vectors one expressing the heavy chain and one expressing the light chain. Optionally, the heavy chain and light chain may be expressed in different host cells.

Additionally, the recombinant expression vector can encode a signal peptide that facilitates secretion of the antibody light and/or heavy chain from a host cell. The antibody light and/or heavy chain gene can be cloned into the vector such that the signal peptide is operably-linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g., IgG$_1$, IgG$_2$, IgG$_3$ and IgG$_4$) or subclass constant region and any allotypic variant thereof as described in Kabat (supra).

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and/or polyoma virus.

Additionally, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NSO) for selection/amplification.

For expression of the light and/or heavy chains, the expression vector(s) encoding the heavy and/or light chains is introduced into a host cell by standard techniques e.g. electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies of the invention include Chinese Hamster Ovary (CHO cells) [including dhfr minus CHO cells, as described in Urlaub and Chasin, Proc. Natl. Acad. Sci. USA 77:4216-20, 1980, used with a DHFR selectable marker, e.g. as described in Kaufman and Sharp, J. Mol. Biol. 159:601-21, 1982], NSO myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

The invention provides a host cell comprising a nucleic acid molecule of the present invention. Preferably a host cell of the invention comprises one or more vectors or constructs comprising a nucleic acid molecule of the present invention. For example, a host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably-linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxyapatite chromatography, gel electrophoresis, and the like. Standard procedures for purification of therapeutic antibodies are described, for example, by Feng L1, Joe X. Zhou, Xiaoming Yang, Tim Tressel, and Brian Lee in an article entitled "Current Therapeutic Antibody Production and Process Optimization" (BioProcessing Journal, September/October 2005)(incorporated by reference in its entirety for purposes of teaching purification of therapeutic antibodies). Additionally, standard techniques for removing viruses from recombinantly expressed antibody preparations are also known in the art (see, for example, Gerd Kern and Mani Krishnan, "Viral Removal by Filtration: Points to Consider" (Biopharm International, October 2006)). The effectiveness of filtration to remove viruses from preparations of therapeutic antibodies is known to be at least in part dependent on the concentration of protein and/or the antibody in the solution to be filtered. The purification process for antibodies of the present invention may include a step of filtering to remove viruses from the mainstream of one or more chromatography operations. Preferably, prior to filtering through a pharmaceutical grade nanofilter to remove viruses, a chromatography mainstream containing an antibody of the present invention is diluted or concentrated to give total protein and/or total antibody concentration of about 1 g/L to about 3 g/L. Even more preferably, the nanofilter is a DV20 nanofilter (e.g., Pall Corporation; East Hills, N.Y.). Substantially pure immunoglobulins of at least about 90%, about 92%, about 94% or about 96% homogeneity are preferred, and about 98 to about 99% or more homogeneity most preferred, for pharmaceutical uses. Once purified, partially or to homogeneity as desired, the sterile antibodies may then be used therapeutically, as directed herein.

In view of the aforementioned discussion, the present invention is further directed to an antibody obtainable by a process comprising the steps of culturing a host cell including, but not limited to a mammalian, plant, bacterial, transgenic animal, or transgenic plant cell which has been transformed by a polynucleotide or a vector comprising nucleic acid molecules encoding antibodies of the invention so that the nucleic acid is expressed and, optionally, recovering the antibody from the host cell culture medium.

In certain aspects, the present application provides hybridoma cell lines, as well as to the monoclonal antibodies produced by these hybridoma cell lines. The cell lines disclosed have uses other than for the production of the monoclonal antibodies. For example, the cell lines can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-ETR immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-ETR light or heavy chain can be isolated (e.g., by PCR) or cDNA libraries can be prepared from mRNA isolated from the cell lines, and cDNA clones encoding an anti-ETR immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host T-cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host T-cell by an appropriate method (e.g., transformation, transfection, electroporation, infection), such that the nucleic acid is operably linked to one or more expression control elements (e.g., in the vector or integrated into the host T-cell genome). For production, host T-cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host T-cells or medium). It will be appreciated that the method of production encompasses expression in a host T-cell of a transgenic animal (see e.g., WO 92/03918, GenPharm International, published Mar. 19, 1992)(incorporated by reference in its entirety).

Host cells can also be used to produce portions, or fragments, of intact antibodies, e.g., Fab fragments or scFv molecules by techniques that are conventional. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to human ETR. The molecules expressed from such truncated DNA molecules are also encompassed by the antibodies of the invention.

Methods for expression of single chain antibodies and/or refolding to an appropriate active form, including single chain antibodies, from bacteria such as *E. coli* have been described and are well-known and are applicable to the antibodies disclosed herein (see, e.g., Buchner et al., Anal. Biochem. 205:263-270, 1992; Pluckthun, Biotechnology 9:545, 1991; Huse et al., Science 246:1275, 1989 and Ward et al., Nature 341:544, 1989, all incorporated by reference herein).

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., Biochemistry 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two-chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after redox shuffling is completed.

In addition to recombinant methods, the antibodies, labeled antibodies and antigen-binding fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

The following examples are offered to more fully illustrate the invention but are not construed as limiting the scope thereof.

Example 1

Generation of Monoclonal Antibodies Targeting Specifically to Human ET$_A$R Balb/c and C57Bl/6 mouse (22 gms, 6-8 weeks old) were each immunized bi-weekly (5 total immunizations) with 100 μg or 50 μg hET$_A$R plasmid DNA with Gene Gun, and splenocytes were harvested 4 days after the final immunization for fusion with myeloma cell line NSO from ATCC (Allendale, N.J.). Electric fusion methods are used to obtain hybridoma cells and then the hybridoma supernatants are screened for antigen binding, ligand blocking, IgG binning, reference antibody binding, and FACS binding. 21 murine mAbs were ultimately selected from the initial screens for subcloning (limited dilution method). BD Cell MAb Medium was used to grow hybridomas in roller bottles for the collection of supernatants for antibody production. mAbs were purified with Protein A affinity chromatography. Estimated purity of mAbs was higher than 90% based on SDS-PAGE Coomassie staining. Secondary screening of the 21 mAbs comprised: human ET$_A$R binding assays (FACS) and evaluation of functional effects in an IP1 assay (IP-one-Gq kit, Cisbio).

To evaluate the functional effects of ET$_A$R, the 21 purified mAbs were assessed in recombinant CHO cells stably expressing ET$_A$R using an IP1 assay (IP-one-Gq kit, Cisbio). To assess antagonist activity, recombinant CHO cells expressing tagged ET$_A$R were added to 96-well half-area white plates (20,000 cells per well) and were treated with EDNRA mAb at 0.5 pM to 1 μM for 30 min at room temperature. 25.0 nM of ET-1 corresponding to the EC80, was then added and cells were further incubated for 30 min at room temperature. The reaction was stopped by adding detection mix to all wells followed by a 60 min incubation at room temperature. The assay plates were read on an EnVision® Multilabel Plate Reader (PerkinElmer; Waltham, Mass., USA) at an emission wavelength of 665 nm. The ratio of HTRF 665/620 is used to indicate the blocking of ligand binding. The lower the ratio, the lower degree of the blockage. All results were analyzed by nonlinear regression curve fit using GraphPad Prism version 6 (GraphPad Inc., La Jolla, Calif.).

Figure 2:
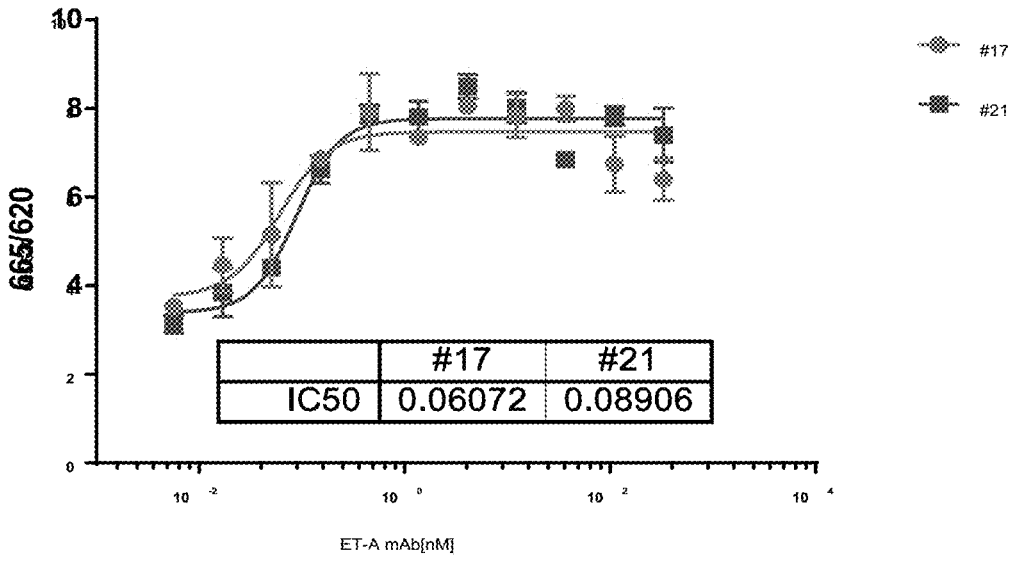
FIG. 2 is a line graph depicting the $ET_AR$ functional assay data (IC50) for murine mAbs #17 (312A10E5 (mAb A3)) and #21 (336D8G9 (mAb A2)).

The functional assay data for 21 mAbs are summarized in FIG. 1. The IC50 of the top two Abs are summarized in FIG. 2 and Table 3:

TABLE 3

| Murine mAb | mAb ID | HuET$_A$R Binding IC50 (nM) |
|---|---|---|
| A2 | 336D8G9 | 0.06072 |
| A3 | 312A10E5 | 0.08906 |

Based on the cumulative results of the binding and secondary assays, purified murine mAb 178D1F6C1G6 ("A1"), mAb 336D8G9 ("A2") and mAb 312A10E5 ("A3") were selected for sequencing and further analysis. Total RNA was extracted from frozen hybridoma cells following the technical manual of TRIzol® Reagent. The total RNA was analyzed by agarose gel electrophoresis. Total RNA was reverse transcribed into cDNA using isotype-specific antisense primers or universal primers following the technical manual of PrimeScript™ 1st Strand cDNA Synthesis Kit. PCR was then performed to amplify the variable regions (heavy and light chains) of the antibodies, which were then cloned into a standard cloning vector separately and sequenced. Murine mAb 178D1F6C1 G6 ("A1"), mAb 336D8G9 ("A2") and mAb 312A10E5 ("A3") comprise the heavy chain variable region sequences set forth in SEQ ID NOs: 19, 23 and 27, respectively, and the light chain variable region sequences set forth in SEQ ID NOs: 21, 25 and 29, respectively. The heavy chain variable regions of mAb 178D1F6C1G6 ("A1"), mAb 336D8G9 ("A2") and mAb 312A10E5 ("A3") are encoded by the nucleic acid sequences set forth in SEQ ID NOs: 20, 24 and 28, respectively, and the light chain variable regions are encoded by the nucleic acid sequences set forth in SEQ ID NOs: 22, 26 and 30, respectively.

Example 2

Generation of a Chimeric IgG Targeting Human ET$_A$R

Using the HCVR and LCVR sequences of mAb 312A10E5 ("A3"), a murine-human IgG chimeric Fab (hereinafter "chimeric IgG") was prepared and which comprised the heavy chain variable region sequence set forth in SEQ ID NO: 31 and the light chain variable region sequence set forth in SEQ ID NO: 32.

The DNA sequences encoding the chimeric IgG heavy and light chains were synthesized and inserted into pTT5 vector to construct the expression plasmids of full-length IgGs. Expression of chimeric IgG was conducted in HEK293 cell culture and the supernatants were purified with protein A affinity column. The purified antibody was buffer-exchanged into PBS using PD-10 desalting column. The concentration and purity of the purified protein were determined by OD280 and SDS-PAGE, respectively. The purified chimeric IgG migrated as ~170 kDa band in SDS-PAGE under non-reducing conditions. Evaluating by the SDS-PAGE result, the purity of the IgGs was >95%.

Example 3

Generation of Humanized Abs Specifically Targeting Human ETR

A CDR grafting and back mutation method was used to prepare humanized anti-ETR mAbs derived from murine mAb 312A10E5 ("A3"). The structure of parental antibody was modelled by computer-aided homology modelling program. Humanized antibodies were designed using CDR grafting and subsequent replaced putative back mutation sites of grafted antibody. Briefly, the CDRs of parental mAb A3 were grafted into the human acceptors to obtain humanized light chains and humanized heavy chains for the parental antibody. The sequences of three humanized heavy chain variable regions (referred to as VH1, VH2, VH3) are set forth in SEQ ID NOs: 33-35, respectively and the sequences of three humanized light chain variable regions (referred to as VL2 and VL3) are set forth in SEQ ID NOs: 36-37, respectively were paired with each other for affinity ranking experiments.

The DNA sequences encoding the chimeric antibody and humanized IgG heavy and light chains were synthesized and inserted into pCDNA3.4 vector to construct the expression plasmids of full-length IgGs. 16 humanized Abs were expressed in Expi293F cell culture, and then the cells were spun down. For affinity ranking, the supernatants were assayed by FACS against cell lines for the assessment of binding activity. Positive cells lines (CCR5/CHO-K1) and negative cells were cultured following the protocol and harvested by centrifugation. About $1\times10^5$ cells per well were washed with 1*PBS and incubated in a serial dilution of antibodies for 30 minutes at 4° C. After washing with PBS, secondary antibody [1 µg/ml Alexa Fluor® 647 AffiniPure Goat Anti-Human IgG (H+L)] was added to the cells and incubated in PBS for 30 minutes at 4° C. After washing with PBS, cells were analyzed for binding by using FACSCalibur™ (BD Bioscience, San Jose, Calif.) and Flowjo software. The antibodies were ranked by EC50. The binders that interact with $ET_AR$ with similar affinity to parental antibody were selected.

Top three binders were selected to express in the Expi293F cell culture. The recombinant plasmids encoding target IgG were transiently co-transfected and the supernatants were purified with protein A affinity column. The purified antibody was buffer exchanged into PBS using dialysis bag. The concentration and purity of the purified protein were determined by OD280 and SDS-PAGE, respectively. Binding confirmation were tested by FACSCalibur™ (BD Bioscience, San Jose, Calif.).

Three IgGs (VH1/VL3), (VH2/VL3) and (VH3/VL3) were selected for expression in the Expi293F cell culture. The recombinant plasmids encoding target IgG were transiently co-transfected and the supernatants were purified with protein A affinity column. The purified antibody was buffer exchanged into PBS using dialysis bag. The concentration and purity of the purified protein were determined by OD280 and SDS-PAGE, respectively. Evaluating from the SDS-PAGE, the purity of humanized IgGs were >95%. Binding confirmation were tested by FACSCalibur™ (BD Bioscience, San Jose, Calif.). The HC and LC amino acid sequences for the 3 selected humanized ETR antibodies are summarized in Table 4:

TABLE 4

| Humanized IgG | HC | LC |
| --- | --- | --- |
| 1 (VH1/VL3) | SEQ ID NO: 38 | SEQ ID NO: 40 |
| 2 (VH2/VL3) | SEQ ID NO: 42 | SEQ ID NO: 40 |
| 3 (VH3/VL3) | SEQ ID NO: 44 | SEQ ID NO: 40 |

Figure 3:
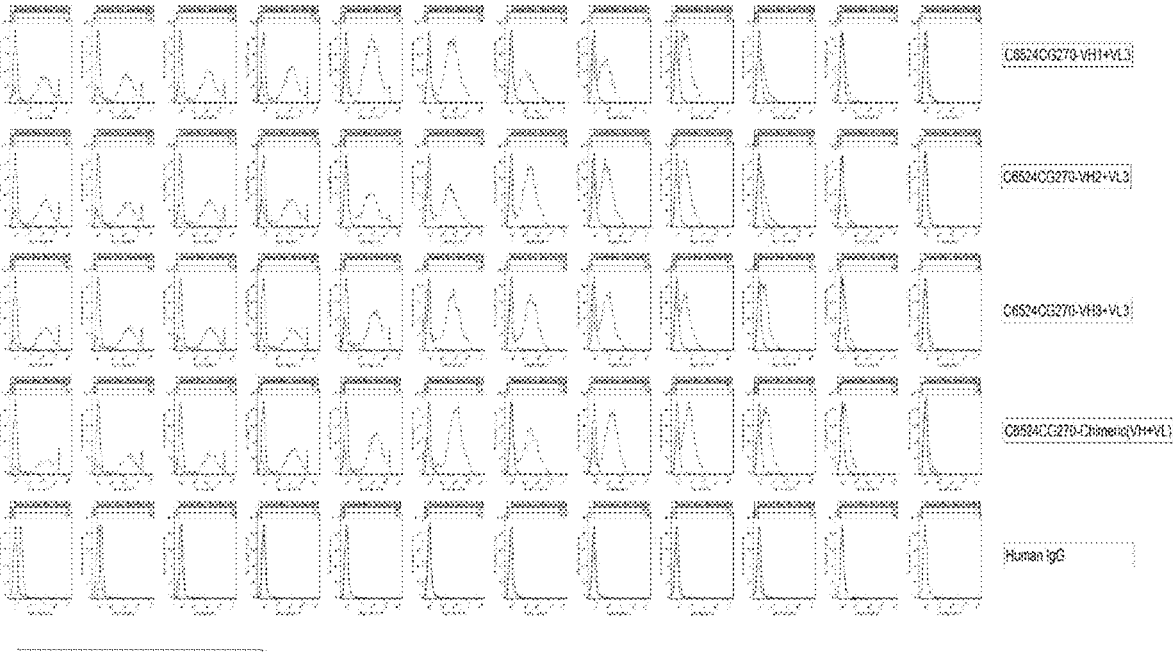
FIG. 3 depict the FACS binding assay data for various $ET_AR$ humanized antibodies.

The FACS binding data is summarized in FIG. 3. All three humanized antibodies demonstrated similar binding affinity as the chimeric antibody.

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Sequence Listings

The nucleic and amino acid sequences listed in the accompanying sequence listing are shown using standard letter abbreviations for nucleotide bases and three letter code for amino acids, as defined in 37 C.F.R. 1.822.

SEQ ID NO: 1 is an amino acid sequence comprising a human $ET_AR$.

SEQ ID NOs: 2-4 are the amino acid sequence of a heavy chain CDR1 in a monoclonal antibody which specifically binds $ET_AR$.

SEQ ID NOs: 5-7 are the amino acid sequences of a heavy chain CDR2 in a monoclonal antibody which specifically binds $ET_AR$.

SEQ ID NOs: 8-10 are the amino acid sequences of a heavy chain CDR3 in a monoclonal antibody which specifically binds $ET_AR$.

SEQ ID NOs: 11-13 are the amino acid sequences of a light chain CDR1 in a monoclonal antibody which specifically binds $ET_AR$.

SEQ ID NO: 14-15 are the amino acid sequences of a light chain CDR2 in a monoclonal antibody which specifically binds $ET_AR$.

SEQ ID NOs: 16-18 are the amino acid sequences of a light chain CDR3 in a monoclonal antibody which specifically binds $ET_AR$.

SEQ ID NOs: 19, 23 and 27 are amino acid sequences of a heavy chain variable region of murine monoclonal antibodies which specifically bind $ET_AR$.

SEQ ID NOs: 20, 24 and 28 are nucleic acid sequences encoding a heavy chain variable region of murine monoclonal antibodies which specifically bind $ET_AR$.

SEQ ID NOs: 21, 25 and 29 are amino acid sequences of a light chain variable region of murine monoclonal antibodies which specifically bind $ET_AR$.

SEQ ID NOs: 22, 26 and 30 are nucleic acid sequences encoding a light chain variable region of murine monoclonal antibodies which specifically bind $ET_AR$.

SEQ ID NO: 31 is the amino acid sequence of a heavy chain variable region of a murine-human chimeric antibody which specifically binds $ET_AR$.

SEQ ID NO: 32 is the amino acid sequence of a light chain variable region of a murine-human chimeric antibody which specifically binds $ET_AR$.

SEQ ID NOs: 33-35 are amino acid sequences of a heavy chain variable regions of humanized monoclonal antibodies which specifically binds $ET_AR$.

SEQ ID NOs: 36-37 are amino acid sequences of a light chain variable regions of humanized monoclonal antibodies which specifically binds $ET_AR$.

SEQ ID NO: 38, 42 and 44 are amino acid sequences of a heavy chain of humanized monoclonal antibodies which specifically binds ET$_A$R.

SEQ ID NOs: 39, 43 and 45 are nucleic acid sequences of a heavy chain of humanized monoclonal antibodies which specifically binds ET$_A$R.

SEQ ID NOs: 40 and 46 are amino acid sequences of a light chain of humanized monoclonal antibodies which specifically binds ET$_A$R.

SEQ ID NOs: 41 and 47 are nucleic acid sequences of a light chain of humanized monoclonal antibodies which specifically binds ET$_A$R.

SEQ ID NOs: 48 and 49 are the amino acid sequences of a light chain constant region of a monoclonal antibody which specifically binds ET$_A$R.

SEQ ID NO: 50 is the amino acid sequence of a heavy chain constant region of a monoclonal antibody which specifically binds ET$_A$R.

Sequence Listings

```
ET_AR amino acid sequence
                              SEQ ID NO: 1
METLCLRASFWLALVGCVISDNPERYSTNLSNHVD

DFTTFRGTELSFLVTTHQPTNLVLPSNGSMHNYCP

QQTKITSAFKYINTVISCTIFIVGMVGNATLLRII

YQNKCMRNGPNALIASLALGDLIYVVIDLPINVFK

LLAGRWPFDHNDFGVFLCKLFPFLQKSSVGITVLN

LCALSVDRYRAVASWSRVQGIGIPLVTAIEIVSIW

ILSFILAIPEAIGFVMVPFEYRGEQHKTCMLNATS

KFMEFYQDVKDWWLFGFYFCMPLVCTAIFYTLMTC

EMLNRRNGSLRIALSEHLKQRREVAKTVFCLVVIF

ALCWFPLHLSRILKKTVYNEMDKNRCELLSFLLLM

DYIGINLATMNSCINPIALYFVSKKFKNCFQSCLC

CCCYQSKSLMTSVPMNGTSIQWKNHDQNNHNTDRS

SHKDSMN

Murine monoclonal antibody heavy
chain
CDR1 amino acid sequence
                              SEQ ID NO: 2
SYWMN Murine monoclonal antibody heavy
chain
CDR1 amino acid sequence
                              SEQ ID NO: 3
DYYIH Murine monoclonal antibody heavy
chain CDR1 amino acid sequence
                              SEQ ID NO: 4
NYGMS Murine monoclonal antibody heavy
chain CDR2 amino acid sequence
                              SEQ ID NO: 5
QIYPGNGDTNYNGKFRG
```

-continued

```
Murine monoclonal antibody heavy
chain CDR2 amino acid sequence
                              SEQ ID NO: 6
RIDPEDGDTEYAPKFQG Murine monoclonal antibody heavy
chain CDR2 amino acid
sequence
                              SEQ ID NO: 7
WINTYSGESTYADDFKG Murine monoclonal antibody heavy
chain CDR3 amino acid
sequence
                              SEQ ID NO: 8
RGSLDY Murine monoclonal antibody heavy
chain CDR3 amino acid
sequence
                              SEQ ID NO: 9
GYTFTNWYSNSY Murine monoclonal antibody heavy
chain CDR3 amino acid
sequence
                              SEQ ID NO: 10
SLNRDTWFTY Murine monoclonal antibody light
chain CDR1 amino acid
sequence
                              SEQ ID NO: 11
KSSHSLVHSNGDTYLH Murine monoclonal antibody light
chain CDR1 amino acid sequence
                              SEQ ID NO: 12
RSSQSLVHSNGNTYLH Murine monoclonal antibody light
                              SEQ ID NO: 13
chain CDR1 amino acid sequence
RSITGAVTTSNYAN Murine monoclonal antibody light
chain CDR2 amino acid sequence
                              SEQ ID NO: 14
KVSNRFS Murine monoclonal antibody light
chain CDR2 amino acid sequence
                              SEQ ID NO: 15
GTNNRAP Murine monoclonal antibody light
chain CDR3 amino acid
sequence
                              SEQ ID NO: 16
SQTTYVPYT Murine monoclonal antibody light
chain CDR3 amino acid
sequence
                              SEQ ID NO: 17
SQSTHVPYT Murine monoclonal antibody light
chain CDR3 amino acid sequence
                              SEQ ID NO: 18
ALWYSNHWV Murine monoclonal antibody heavy
chain variable region amino acid
sequence
                              SEQ ID NO: 19
QVQLQQSGAELVRPGSSVRISCKAFDYAFSSYWMN

WVKQRPGQDLEWIGQIYPGNGDTNYNGKFRGKASL
```

-continued

TADKSSSTAYMHLSSLTSEDSAVYFCARRGSLDYW

GQGTSVTVSS

Murine monoclonal antibody heavy
chain variable region nucleic acid
sequence
                                SEQ ID NO: 20
caggttcagctgcagcagtctggggctgagttggt gaggcctgggtcctcagtgaggatttcctgcaagg cttttgactatgcattcagtagctactggatgaac tgggtgaagcagaggcctggacaggatcttgagtg gattggacagatttatcctggaaatggtgatacta actacaatggaaagttcagggggtaaagcctcactg actgcagacaaatcctccagcacagcctacatgca cctcagcagcctaacatctgaggactctgcggtct atttctgtgcaagacggggggtctttggactactgg ggtcaaggaacctcagtcaccgtctcctca Murine monoclonal antibody light
chain variable region amino acid
sequence
                                SEQ ID NO: 21
DVVMTQIPLSLPVSLGDQSSISCKSSHSLVHSNGD

TYLHWFLQKPGQSPKLLIYKVSNRFSGVPDRFTGS

GSGTEFTLKISRVEAEDLGVYFCSQTTYVPYTFGG

GTKLEIK

Murine monoclonal antibody light
chain variable region nucleic acid
sequence
                                SEQ ID NO: 22
gatgtggtgatgacccaaattccactctccctgcc tgtcagtcttggagatcaatcctccatctcttgca aatctagtcatagccttgtacatagtaatggagac acctatttacattggttcctgcagaagccaggcca gtctccaaagctcctgatctacaaagtctccaacc gattttctggggtcccagacaggttcactggcagt ggttcagggacagagttcacactcaagatcagcag agtggaggctgaggatctgggagtttatttctgct ctcaaactacatatgttccgtacacgttcggaggg gggaccaagctggaaataaaa Murine monoclonal antibody heavy
chain variable region amino acid
sequence
                                SEQ ID NO: 23
EVQLQQSGAELVRPGASVKLSCPASGFTIKDYYIH

WVKQRPEQGLEWIGRIDPEDGDTEYAPKFQGKATM

TADTSSNTAYLHLSSLTSEDTAVYYCTSNWYSNSY

WGQGTTLTVSS

-continued

Murine monoclonal antibody heavy
chain variable region nucleic acid
sequence
                                SEQ ID NO: 24
gaggttcagctgcagcagtctggggcagagcttgt gaggccagggGcctcagtcaagttgtcctgcccag cttctggcttcaccattaaagactactatatacac tgggtgaagcagaggcctgagcagggcctggagtg gattggaaggattgatcctgaggatggtgatactg aatatgccccgaagttccagggcaaggccactatg actgcagacacatcctccaacacagcctacctgca cctcagcagcctgacatctgaggacactgccgtct attactgtacttcaaactggtatagtaactcctac tggggccaaggcaccactctcacagtctcctca Murine monoclonal antibody light
chain variable region amino acid
sequence
                                SEQ ID NO: 25
DVVMTQTPLSLPVSLGDQASISCRSSQSLVHSNGN

TYLHWYLQKPGQSPKVLIYKVSNRFSGVPDRFSGS

GSGTDFTLKISRVEAEDLGVYFCSQSTHVPYTFGG

GTKLEIK

Murine monoclonal antibody light
chain variable region nucleic acid
sequence
                                SEQ ID NO: 26
gatgttgtgatgacccaaactccactctccctgcc tgtcagtcttggagatcaagcctccatctcttgca gatctagtcagagccttgtacacagtaatggaaac acctatttacattggtacctgcaaaagccaggcca gtctccaaaggtcctgatctacaaagtttccaacc gattttctggggtcccagacaggttcagtggcagt ggatcagggacagatttcacactcaagatcagcag agtggaggctgaggatctgggagtttatttctgct ctcaaagtacacatgttccgtatacgttcggaggg gggaccaagctggaaataaaa Murine monoclonal antibody heavy
chain variable region amino acid
sequence
                                SEQ ID NO: 27
QIQLVQSGPDLKKPGETVKISCKASGYTFTNYGMS

WVKQAPGKGLKWMGWINTYSGESTYADDFKGRFAF

SLETSASTAYLQINNLKNEDTATYFCARSLNRDTW

FTYWGQGTLVTVSA

Murine monoclonal antibody heavy
chain variable region nucleic acid
sequence
                                SEQ ID NO: 28
cagatccagttggtacagtctggacctgacctgaa gaagcctggagagacagtcaagatctcctgcaagg -continued cttctgggtataccttcacaaactatggaatgagc tgggtgaaacaggctccaggaaagggtttaaagtg gatgggctggataaacacctattctggagagtcaa catatgctgatgacttcaagggacggttttgccttc tctttggaaacctctgccagcactgcctatttgca gatcaacaacctcaaaaatgaggacacggctacat atttctgtgcaagatccctcaaccgggacacctgg tttacttactggggccaagggactctggtcactgt ctctgca Murine monoclonal antibody light
chain variable region amino acid
sequence
SEQ ID NO: 29
QAVVTQESALSTSPGETVTLTCRSITGAVTTSNYA

NWVQEKPDHLFTGLIGGTNNRAPGVPARFSGSLIG

DKAALTITGAQTEDEAIYFCALWYSNHWVFGGGTK

LTVL

Murine monoclonal antibody light
chain variable region nucleic acid
sequence
SEQ ID NO: 30
caggctgttgtgactcaggaatctgcactctccac atcacctggtgaaacagtcacactcacttgtcgct caattactggggctgttacaactagtaactatgcc aactgggtccaagaaaaaccagatcatttgttcac tggtctaataggtggtaccaacaaccgagctccag gtgttcctgccagattctcaggctccctgattgga gacaaggctgccctcaccatcacagggggcacagac tgaggatgaggcaatatatttctgtgctctatggt acagcaaccactgggtgttcggtggaggaaccaaa ctgactgtccta Heavy chain variable region amino acid
sequence of a murine-human
chimeric antibody
SEQ ID NO: 31
QVQLVQSGAEVKKPGASVKVSCKASGYTFTNYGMS

WVRQAPGQGLEWMGWINTYSGESTYADDFKGRVTM

TTDTSTSTAYMELRSLRSDDTAVYYCARSLNRDTW

FTYWGQGTLVTVSS

Light chain variable region amino acid
sequence of a murine-human chimeric
antibody
SEQ ID NO: 32
QTVVTQEPSFSVSPGGTVTLTCRSITGAVTTSNYA

NWYQQTPGQAPRTLIYGTNNRAPGVPDRFSGSILG

NKAALTITGAQADDESDYYCALWYSNHWVFGGGTK

LTVL

-continued

Humanized heavy chain variable
region amino acid sequence
SEQ ID NO: 33
QVQLVQSGAEVKKPGASVKVSCKASGYTFTNYGMSW

VRQAPGQGLEWMGWINTYSGESTYADDFKGRVTMT

TDTSTSTAYMELRSLRSDDTAVYYCARSLNRDTWF

TYWGQGTLVTVSS

Humanized heavy chain variable
region amino acid sequence
SEQ ID NO: 34
QVQLVQSGAEVKKPGASVKVSCKASGYTFTNYGMS

WVRQAPGQGLEWMGWINTYSGESTYADDFKGRFTM

TLDTSTSTAYMELRSLRSDDTAVYFCARSLNRDTW

FTYWGQGTLVTVSS

Humanized heavy
chain variable region amino acid
sequence
SEQ ID NO: 35
QVQLVQSGAEVKKPGASVKVSCKASGYTFTNYGMS

WVRQAPGQGLEWMGWINTYSGESTYADDFKGRFTF

TLDTSTSTAYMELRSLRSDDTATYFCARSLNRDTW

FTYWGQGTLVTVSS

Humanized light chain variable
region amino acid sequence
SEQ ID NO: 36
QTVVTQEPSFSVSPGGTVTLTCRSITGAVTTSNYA

NWYQQTPGQAPRGLIGGTNNRAPGVPDRFSGSILG

NKAALTITGAQADDESDYFCALWYSNHWVFGGGTK

LTVL

Humanized light chain variable
region amino acid sequence
SEQ ID NO: 37
QTVVTQEPSFSVSPGGTVTLTCRSITGAVTTSNYA

NWVQETPGQAPRGLIGGTNNRAPGVPDRFSGSILG

NKAALTITGAQADDEADYFCALWYSNHWVFGGGTK

LTVL

Humanized heavy chain amino acid
sequence
SEQ ID NO: 38
QVQLVQSGAEVKKPGASVKVSCKASGYTFTNYGMS

WVRQAPGQGLEWMGWINTYSGESTYADDFKGRVTM

TTDTSTSTAYMELRSLRSDDTAVYYCARSLNRDTW

FTYWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

-continued

NGQPENNYKTTPPVLDSDGSFFLYSKLTVDKSRWQ

QGNVFSCSVMHEALHNHYTQKSLSLSPGK

Humanized heavy chain nucleic acid
sequence
SEQ ID NO: 39
caggtgcagctggtgcagtctggagcagaggtgaa gaagccaggagcctctgtgaaggtgagctgcaagg cctccggctacaccttcacaaactatggcatgagc tgggtgcggcaggcacctggacagggactggagtg gatgggctggatcaatacatactccggcgagtcta cctatgccgacgacttcaagggcagggtgacaatg accacagacacctctacaagcaccgcctacatgga gctgcggagcctgagatccgacgataccgccgtgt actattgtgccaggtccctgaaccgcgatacatgg ttcacctattggggccagggcacactggtgaccgt gagctccgccagcaccaagggcccttccgtgtttc cactggccccctcctctaaatccacatctggcggc accgccgccctgggctgtctggtgaaggactactt cccagagcctgtgacagtgtcctggaactctggcg ccctgacatccggcgtgcacacatttccagccgtg ctgcagagctccggcctgtacagcctgtctagcgt ggtgacagtgccctcctctagcctgggcacacaga cctatatctgcaacgtgaatcacaagccaagcaat accaaggtggacaagaaggtggagcccaagtcctg tgataagacacacacctgccccccttgtcctgctc ccgagctgctgggcggccctagcgtgttcctgttt ccacccaagcctaaggacaccctgatgatctcccg gacacccgaggtgacctgcgtggtggtggacgtgt ctcacgaggatcctgaggtgaagttcaactggtat gtggatggcgtggaggtgcacaatgccaagaccaa gcccagagaggagcagtacaactctacatataggg tggtgagcgtgctgaccgtgctgcaccaggactgg ctgaacggcaaggagtataagtgcaaggtgtccaa taaggccctgcccgcccccatcgagaagacaatca gcaaggccaagggccagcctcgggagccacaggtg tacaccctgcctccatccagagacgagctgacaaa gaaccaggtgtctctgacatgtctggtgaagggct tctatcctagcgatatcgccgtggagtgggagtcc aatggccagccagagaacaattacaagaccacacc ccctgtgctggactccgatggctccttcttcctgt attccaagctgaccgtggataagtctcggtggcag cagggcaacgtgttcagctgttccgtgatgcacga -continued agccctgcataatcactatactcagaaatccctgt ccctgtcacctggaaag Humanized light chain amino acid
sequence
SEQ ID NO: 40
QTVVTQEPSFSVSPGGTVTLTCRSITGAVTTSNYA

NWVQETPGQAPRGLIGGTNNRAPGVPDRFSGSILG

NKAALTITGAQADDEADYFCALWYSNHWVFGGGTK

LTVLGQPKAAPSVTLFPPSSEELQANKATLVCLIS

DFYPGAVTVAWKADSSPVKAGVETTTPSKQSNNKY

AASSYLSLTPEQWKSHRSYSCQVTHEGSTVEKTVA

PTECS

Humanized light chain nucleic acid
sequence
SEQ ID NO: 41
cagacagtggtgacccaggagcctagcttctccgt gtctccaggaggaaccgtgacactgacctgcaggt ctatcacaggcgccgtgaccacaagcaactacgcc aattgggtgcaggagacaccaggacaggcaccaag gggactgatcggaggaaccaacaatagggcaccag gagtgcctgaccggttcagcggatccatcctggga aacaaggccgccctgacaatcaccggagcacaggc agacgatgaggcagattacttctgtgccctgtggt attccaatcactgggtgtttggcggcggcacaaag ctgaccgtgctggggcagcccaaggccgctcctag cgtgacactgtttcccccttcctccgaggagctgc aggccaacaaggccaccctggtgtgcctgatctcc gacttctatcctggcgccgtgacagtggcctggaa ggctgattctagcccagtgaaggctggcgtggaga ccacaaccccctccaagcagtctaacaataagtat gccgcttcctcttacctgagcctgacaccagagca gtggaagtcccaccggtcttacagctgccaggtca ctcacgaaggctctaccgtggaaaagacagtcgca cccaccgaatgctcatgataagcttaagggttcga tccct Humanized heavy chain amino acid
sequence
SEQ ID NO: 42
QVQLVQSGAEVKKPGASVKVSCKASGYTFTNYGMS

WVRQAPGQGLEWMGWINTYSGESTYADDFKGRFTM

TLDTSTSTAYMELRSLRSDDTAVYFCARSLNRDTW

FTYWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

-continued

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK

Humanized heavy chain nucleic acid
sequence
                        SEQ ID NO: 43
caggtgcagctggtgcagtctggagcagaggtgaa gaagccaggagcctctgtgaaggtgagctgcaagg cctccggctacaccttcacaaactatggcatgagc tgggtgcggcaggcacctggacagggactggagtg gatgggctggatcaatacatactccggcgagtcta cctatgccgacgatttcaagggcaggtttaccatg acactggacacctctacaagcaccgcctacatgga gctgcggagcctgagatccgacgatacagccgtgt atttctgtgccaggtccctgaaccgcgatacatgg tttacctactggggccagggcacactggtgaccgt gagctccgccagcaccaagggcccttccgtgtttc cactggccccctcctctaaatccacatctggcggc accgccgccctgggctgtctggtgaaggactactt cccagagcctgtgacagtgtcctggaactctggcg ccctgacatccggcgtgcacacatttccagccgtg ctgcagagctccggcctgtacagcctgtctagcgt ggtgacagtgccctcctctagcctgggcacacaga cctatatctgcaacgtgaatcacaagccaagcaat accaaggtggacaagaaggtggagcccaagtcctg tgataagacacacacctgcccccccttgtcctgctc ccgagctgctgggcggccctagcgtgttcctgttt ccacccaagcctaaggacaccctgatgatctcccg gacacccgaggtgacctgcgtggtggtggacgtgt ctcacgaggatcctgaggtgaagttcaactggtat gtggatggcgtggaggtgcacaatgccaagaccaa gcccagagaggagcagtacaactctacatataggg tggtgagcgtgctgaccgtgctgcaccaggactgg ctgaacggcaaggagtataagtgcaaggtgtccaa taaggccctgccgcccccatcgagaagacaatca gcaaggccaagggccagcctcgggagccacaggtg tacaccctgcctccatccagagacgagctgacaaa gaaccaggtgtctctgacatgtctggtgaagggct tctatcctagcgatatcgccgtggagtgggagtcc -continued aatggccagccagagaacaattacaagaccacacc ccctgtgctggactccgatggctccttctttctgt attccaagctgaccgtggataagtctcggtggcag cagggcaacgtgttcagctgttccgtgatgcacga agccctgcataatcactatactcagaaatccctgt ccctgtcacctggaaag Humanized heavy chain amino acid
sequence
                        SEQ ID NO: 44
QVQLVQSGAEVKKPGASVKVSCKASGYTFTNYGMS

WVRQAPGQGLEWMGWINTYSGESTYADDFKGRFTF

TLDTSTSTAYMELRSLRSDDTATYFCARSLNRDTW

FTYWGQGTLVTVSSASTKGPSVFPLAPSSKSTSGG

TAALGCLVKDYFPEPVTVSWNSGALTSGVHTFPAV

LQSSGLYSLSSVVTVPSSSLGTQTYICNVNHKPSN

TKVDKKVEPKSCDKTHTCPPCPAPELLGGPSVFLF

PPKPKDTLMISRTPEVTCVVVDVSHEDPEVKFNWY

VDGVEVHNAKTKPREEQYNSTYRVVSVLTVLHQDW

LNGKEYKCKVSNKALPAPIEKTISKAKGQPREPQV

YTLPPSRDELTKNQVSLTCLVKGFYPSDIAVEWES

NGQPENNYKTTPPVLDSDGSFFLYSKLTVDKSRWQ

QGNVFSCSVMHEALHNHYTQKSLSLSPGK

Humanized heavy chain nucleic
acid sequence
                        SEQ ID NO: 45
caggtgcagctggtgcagtctggagcagaggt gaagaagccaggagcctctgtgaaggtgagctgca aggcctccggctacaccttcacaaactatggcatg agctgggtgcggcaggcacctggacagggactgga gtggatgggctggatcaatacatactccggcgagt ctacctatgccgacgacttcaagggcaggttcacc tttacactggacacctctacaagcaccgcctacat ggagctgcggagcctgagatccgacgatacagcca cctatttctgtgccaggtccctgaaccgcgataca tggtttacctactggggccagggcacactggtgac cgtgagctccgccagcaccaagggcccttccgtgt ttccactggccccctcctctaaatccacatctggc ggcaccgccgccctgggctgtctggtgaaggacta cttcccagagcctgtgacagtgtcctggaactctg gcgccctgacatccggcgtgcacacatttccagcc gtgctgcagagctccggcctgtacagcctgtctag cgtggtgacagtgccctcctctagcctgggcacac agacctatatctgcaacgtgaatcacaagccaagc -continued aataccaaggtggacaagaaggtggagcccaagtc ctgtgataagacacacacctgcccccccttgtcctg ctcccgagctgctgggcggccctagcgtgttcctg tttccacccaagcctaaggacaccctgatgatctc ccggacaccgaggtgacctgcgtggtggtggacg tgtctcacgaggatcctgaggtgaagttcaactgg tatgtggatggcgtggaggtgcacaatgccaagac caagcccagagaggagcagtacaactctacatata gggtggtgagcgtgctgaccgtgctgcaccaggac tggctgaacggcaaggagtataagtgcaaggtgtc caataaggccctgcccgcccccatcgagaagacaa tcagcaaggccaagggccagcctcgggagccacag gtgtacacctgcctccatccagagacgagctgac aaagaaccaggtgtctctgacatgtctggtgaagg gcttctatcctagcgatatcgccgtggagtgggag tccaatggccagccagagaacaattacaagaccac acccctgtgctggactccgatggctccttctttc tgtattccaagctgaccgtggataagtctcggtgg cagcagggcaacgtgttcagctgttccgtgatgca cgaagccctgcataatcactatactcagaaatccc tgtccctgtcacctggaaag Humanized light chain amino acid
sequence

SEQ ID NO: 46

QTVVTQEPSFSVSPGGTVTLTCRSITGAVTTSNYA

NWYQQTPGQAPRGLIGGTNNRAPGVPDRFSGSILG

NKAALTITGAQADDESDYFCALWYSNHWVFGGGTK

LTVLGQPKAAPSVTLFPPSSEELQANKATLVCLIS

DFYPGAVTVAWKADSSPVKAGVETTTPSKQSNNKY

AASSYLSLTPEQWKSHRSYSCQVTHEGSTVEKTVA

PTECS

Humanized light chain nucleic acid
sequence

SEQ ID NO: 47 cagacagtggtgacccaggagcctagcttctccgt gtctccaggaggaaccgtgacactgacctgcaggt ctatcacaggcgccgtgaccacaagcaactacgcc aattggtatcagcagacaccaggacaggcaccaag gggactgatcggaggaaccaacaatagggcaccag gagtgcctgaccggttcagcggatccatcctggga aacaaggccgccctgacaatcaccggagcacaggc agacgatgagtccgattacttctgtgccctgtggt attctaatcactgggtgtttggcggcggcacaaag ctgaccgtgctggggcagcccaaggccgctcctag -continued cgtgacactgtttcccccttcctccgaggagctgc aggccaacaaggccaccctggtgtgcctgatctcc gacttctatcctggcgccgtgacagtggcctggaa ggctgattctagcccagtgaaggctggcgtggaga ccacaaccccctccaagcagtctaacaataagtat gccgcttcctcttacctgagcctgacaccagagca gtggaagtcccaccggtcttacagctgccaggtca ctcacgaaggctctaccgtggaaaagacagtcgca cccaccgaatgctcatgataagcttaaggggttcga tccct Light chain constant region
amino acid sequence

SEQ ID NO: 48

RTVAAPSVFIFPPSDEQLKSGTASVVCLLNNFYPR

EAKVQWKVDNALQSGNSQESVTEQDSKDSTYSLSS

TLTLSKADYEKHKVYACEVTHQGLSSPVTKSFNRG

EC

Light chain constant region
amino acid sequence

SEQ ID NO: 49

GQPKAAPSVTLFPPSSEELQANKATLVCLISDFYP

GAVTVAWKADSSPVKAGVETTTPSKQSNNKYAASS

YLSLTPEQWKSHRSYSCQVTHEGSTVEKTVAPTEC

S

Heavy chain constant region
amino acid sequence

SEQ ID NO: 50

ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSRDELTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK

What is claimed is:

1. An isolated antibody or antigen-binding fragment thereof which comprises: (a) a light chain CDR1 sequence identical to SEQ ID NO: 13; (b) a light chain CDR2 sequence identical to SEQ ID NO: 15; (c) a light chain CDR3 sequence identical to SEQ ID NO: 18; (d) a heavy chain CDR1 sequence identical to SEQ ID NO: 4; (e) a heavy chain CDR2 sequence identical to SEQ ID NO: 7; and (f) a heavy chain CDR3 sequence identical to SEQ ID NO: 10.

2. An isolated antibody or antigen-binding fragment thereof according to claim 1, further comprising a set of four variable region framework regions from a human immunoglobulin (IgG).

3. An isolated antibody or antigen-binding fragment thereof according to claim 1 that binds to CGRP protein with a dissociation constant ($K_D$) selected from a $K_D$ of $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, and er at least about $1 \times 10^{-12}$ M.

4. An isolated antibody or antigen-binding fragment thereof according to claim 1 wherein the antibody or antigen-binding fragment is selected from a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, a Fab' fragment, a Fab$_2$ fragment, a F(ab)'$_2$ fragment, a domain antibody, an IgD antibody, an IgE antibody, an IgM antibody, an IgG1 antibody, an IgG2 antibody, an IgG3 antibody, an IgG4 antibody, or an IgG4 antibody having at least one mutation in the hinge region that alleviates a tendency to form intra H-chain disulfide bonds.

5. An isolated humanized antibody or antigen-binding fragment thereof according to claim 4 which comprises the heavy chain variable region sequence set forth in SEQ ID NOs: 27, and the light chain variable region sequence set forth in SEQ ID NOs: 29.

6. An isolated humanized antibody or antigen-binding fragment thereof that specifically binds to human $ET_AR$ and is selected from the group consisting of an antibody which comprises the heavy chain sequence set forth in SEQ ID NO: 38, and the light chain sequence set forth in SEQ ID NO: 40, an antibody which comprises the heavy chain sequence set forth in SEQ ID NO: 42, and the light chain sequence set forth in SEQ ID NO: 40, and an antibody which comprises the heavy chain sequence set forth in SEQ ID NO: 44, and the light chain sequence set forth in SEQ ID NO: 40.

7. A pharmaceutical composition comprising an isolated antibody or antigen-binding fragment thereof according to claim 1 in admixture with a pharmaceutically acceptable carrier.

* * * * *